US010098967B2

(12) United States Patent
Parquette et al.

(10) Patent No.: US 10,098,967 B2
(45) Date of Patent: Oct. 16, 2018

(54) SELF-ASSEMBLY OF THERAPEUTIC AGENT-PEPTIDE NANOSTRUCTURES

(71) Applicants:Ohio State Innovation Foundation, Columbus, OH (US); Trustees of Boston University, Boston, MA (US)

(72) Inventors: Jonathan R. Parquette, Columbus, OH (US); Se Hye Kim, Columbus, OH (US); Mark W. Grinstaff, Brookline, MA (US); Jonah A. Kaplan, Newton, MA (US)

(73) Assignees: Ohio State Innovation Foundation, Columbus, OH (US); Trustees of Boston University, Boston, MA (US)

( * ) Notice: Subject to any disclaimer, the term of this patent is extended or adjusted under 35 U.S.C. 154(b) by 53 days.

(21) Appl. No.: 14/095,816

(22) Filed: Dec. 3, 2013

(65) Prior Publication Data

US 2014/0155577 A1 Jun. 5, 2014

Related U.S. Application Data

(60) Provisional application No. 61/732,655, filed on Dec. 3, 2012.

(51) Int. Cl.
*A61K 47/62* (2017.01)
*A61K 47/54* (2017.01)

(52) U.S. Cl.
CPC ............ *A61K 47/62* (2017.08); *A61K 47/542* (2017.08)

(58) Field of Classification Search
None
See application file for complete search history.

(56) References Cited

U.S. PATENT DOCUMENTS

| | | | |
|---|---|---|---|
| 6,960,648 B2 | 11/2005 | Bonny | |
| 2002/0035243 A1 | 3/2002 | Imfeld et al. | |
| 2002/0120100 A1 | 8/2002 | Bonny | |
| 2003/0032594 A1 | 2/2003 | Bonny | |
| 2006/0275371 A1* | 12/2006 | Dai | A61K 47/48869 424/489 |
| 2010/0144647 A1* | 6/2010 | Kratz et al. | 514/18 |
| 2014/0155577 A1* | 6/2014 | Parquette et al. | 530/330 |

FOREIGN PATENT DOCUMENTS

CN  101618221  *  1/2010

OTHER PUBLICATIONS

Scheeren et al., Novel 20-carbonate linked prodrugs of camptothecin and 9-aminocamptothecin designed for activation by tumour-associated plasmin. Bioorg Med Chem Lett 2002, 12, 2371-2376.*

Cao et al., Alkyl esters of Camptothecin and 9-nitrocamptothecin: Synthesis, in vitro pharmacokinetics, toxicity, and antitumor activity. J Med Chem 1998, 41, 31.*
Mieszawska et al., Multifunctional Gold Nanoparticles for Diagnosis and Therapy of Disease, Mol. Pharm., 10:831-847, 2013.
Miyazawa et al., The Infrared Spectra of Polypeptides in Various Conformations : Amide I and II Bands, J. Am. Chem. Soc., 83:712, 1961.
Moghimi et al., Factors Controlling Nanoparticle Pharmacokinetics: An Integrated Analysis and Perspective, Annu. Rev. Pharmacol., 52:481-503, 2012.
Nabiev, Spectroscopic and Biochemical Characterisation of Self-Aggregates Formed by Antitumor Drugs of the Camptothecin Family, Biochem. Pharmacol., 55:1163-1174, 1998.
Nel et al., Toxic Potential of Materials at the Nanolevel. Science, 311:622-627, 2006.
Ouyang et al., Selective Bone Targeting 5-Fluorouracil Prodrugs: Synthesis and Preliminary Biological Evaluation. Bioorg. & Med. Chem., 19:750-3756, 2011.
Park et al., Polymeric nanomedicine for cancer therapy. Prog Polym Sci, 33:113, 2008.
Patil et al., Engineered nanocarriers of doxorubicin: A current update. Crit Rev Ther Drug, 25:1, 2008.
Potmesil, Camptothecins: from Bench Research to Hospital Wards. Cancer Res, 54:1431, 1994.
Peng et al., Targeted magnetic iron oxide nanoparticles for tumor imaging and therapy, Int. J. Nanomed., 3:311-321, 2008.
Riehemann et al., Nanomedicine—Challenge and Perspectives, Angew Chem Int Edit, 48:872, 2009.
Rothenberg et al., Phase I dose-finding and pharmacokinetic trial of irinotecan (CPT-11) administered every two weeks, Ann. Oncol., 12:1631-1641, 2001.
Rothenberg et al., Phase I and Pharmacokinetic Trial of Weekly CPT-11J. Clin. Oncol., 11:2194-2204, 1993.
Safavy et al., Site-Specifically Traced Drug Release and Biodistribution of a Paclitaxel-Antibody Conjugate Toward Improvement of the Linker Structure. Bioconjugate Chem., 15:1264, 2004.
Saltz et al., The Camptothecins, Lancet, 361:2235-2242, 2003.
Satchi-Fainaro et al., Polymer therapeutics for cancer: Current status and future challenges. Adv Polym Sci, 193:1, 2006.
Scheeren et al., Novel 20-carbonate linked prodrugs of camptothecin and 9-aminocamptothecin designed for activation by tumour-associated plasmin. Bioorg Med Chem Lett, 12:2371, 2002.
Schleich et al., Dual anticancer drug/superparamagnetic iron oxide-loaded PLGA-based nanoparticles for cancer terapy and magnetic resonance imaging, Int. J. Pharm., 447:94-101, 2013.
Shao et al., Aqueous Self-Assembly of L-Lysine-Based Amphiphiles into 1D n-Type Nanotubes. Chem-Eur J, 17:12882, 2011.

(Continued)

*Primary Examiner* — Maury A Audet
(74) *Attorney, Agent, or Firm* — Meunier Carlin & Curfman LLC

(57) ABSTRACT

Disclosed are conjugates of hydrophobic drugs linked to protected or unprotected amino acids or peptides. The disclosed conjugates are amphiphilic and can self assemble into nantubes. Nanotubes comprising the conjugates are also described and can have high loading of the drug and protect it from degradation or elimination. The nanotubes are well suited to deliver hydrophobic and unstable drugs to individuals.

7 Claims, 8 Drawing Sheets
Specification includes a Sequence Listing.

(56) References Cited

OTHER PUBLICATIONS

Shao et al., A pi-conjugated hydrogel based on an Fmoc-dipeptide naphthalene diimide semiconductor. Chem Commun, 46:4285, 2010.
Shao et al., Coupled Conformational Equilibria in â-Sheet Peptide-Dendron Conjugates, J. Am. Chem. Soc., 129:1884-1885, 2007.
Shao et al., Self-Assembly of 1-D n-Type Nanostructures Based on Naphthalene Diimide-Appended Dipeptides, J. Am. Chem. Soc., 131:16374-16376, 2009.
Shen et al., Prodrugs Forming High Drug Loading Multifunctional Nanocapsules for Intracellular Cancer Drug Delivery. J Am Chem Soc, 132:4259, 2010.
Shvedova et al., Exposure to Carbon Nanotube Material: Assessment of Nanotube Cytotoxicity Using Human Keratinocyte Cells. J. Toxicol. Env. Heal., 66:1909-1926, 2003.
Sinka et al., Tumor-targeted bioconjugate based delivery of camptothecin: design, synthesis and in vitro evaluation. J Control Release, 100:275, 2004.
Song et al., A molecular hydrogel of a camptothecin derivative, Biomater. Sci., 1:190-193, 2013.
Soukasene et al., Antitumor Activity of Peptide Amphiphile Nanofiber-Encapsulated Camptothecin ACS Nano, 5:9113-9121, 2011.
Soussan et al., Drug Delivery by Soft Matter: Matrix and Vesicular Carriers. Angew Chem Int Edit, 48:274, 2009.
Subramani et al., Targeting Nanoparticles as Drug Delivery Systems for Cancer Treatment. Curr Nanosci, 5:135, 2009.
Standley et al., Induction of Cancer Cell Death by Self-assembling Nanostructures Incorporating a Cytotoxic Peptide, Cancer Res. ,70:3020-3026, 2010.
Svenson, Theranostics: Are We There Yet?, Mol. Pharmaceut., 10:848-856, 2013.
Ta, et al., Thermosensitive liposomes for localized delivery and triggered release of chemotherapy, J. Control Release, 169:112-125, 2013.
Vishnuvajjala et al., Tricyclo[4.2.2.02,5]Dec-9-Ene-3,4,7,8-Tetracarboxylic Acid Diimide—Formulation and Stability Studies. J Pharm Sci, 75:301, 1986.
Volodkin et al., Near-IR Remote Release from Assemblies of Liposomes and Nanoparticles. Angew Chem Int Edit, 48:1807, 2009.
Wang et al., Nanoparticle Delivery of Cancer Drugs, Annu. Rev. Med., 63:185-198, 2012.
Watanabe et al., Preparation of camptothecin-loaded polymeric micelles and evaluation of their incorporation and circulation stability. Int J Pharm, 308:183, 2006.
Yang et al., Novel camptothecin derivatives. Part 1: Oxyalkanoic acid esters of Camptothecin and their in vitro and in vivo antitumor activity. Bioorg Med Chem Lett, 12:1241, 2002.
Yang et al., Anion effect on the nanostructure of a metal ion binding self-assembling peptide. Langmuir, 22:8553, 2006.
Yu et al., Antitumor activity of poly(ethylene glycol)-Camptothecin conjugate: The inhibition of tumor growth in vivo. J Control Release, 110:90, 2005.
Zhang et al., Polymeric Core-Shell Assemblies Mediated by Host-Guest Interactions: Versatile Nanocarriers for Drug Delivery. Angew Chem Int Edit, 48:964, 2009.
Zhang et al., Host-guest interactions mediated nano-assemblies using cyclodextrin-containing hydrophilic polymers and their biomedical applications, Nano Today, 5:337-350, 2010.
Zhang et al., Poly(ethylene oxide)-block-polyphosphester-based paclitaxel conjugates as a platform for ultra-high paclitaxel-loaded multifunctional nanoparticles, Chem. Sci., 4:2122-2126, 2013.
Zhang et al., Development and characterization of a novel liposome-based formulation of Sn-38 Int. J. Pharm., 270:93-107, 2004.
Zhuo et al., in Vitro Release of 5-Fluorouracil with Cyclic Core Dendritic Polymer. J. Controlled Release, 57:249-257, 1999.
Zullig et al., Cancer Incidence among Patients of the U.S. Veterans Affairs Health Care System. Mil. Med., 177:693-701, 2012.
Ambade et al., Dendrimeric micelles for controlled drug release and targeted delivery. Mol Pharmaceut, 2:264-272, 2005.
Audus et al., Chemical modification of paclitaxel (Taxol) reduces P-glycoprotein interactions and increases permeation across the blood-brain barrier in vitro and in situ. J Med Chem, 48:832-838, 2005.
Beretta et al., Relevance of extracellular and intracellular interactions of camptothecins as determinants of antitumor activity, Biochem. Pharmacol., 74:1437-1444, 2007.
Blanco et al., Molecular-targeted nanotherapies in cancer: Enabling treatment specificity, Mol. Oncol.,5:492-503, 2011.
Boncel et al., Liberation of drugs from multi-wall carbon nanotube carriers, Control. Release, 169:126-140, 2013.
Borgman et al., Targetable HPMA Copolymer-Aminohexylgeldanamycin Conjugates for Prostate Cancer Therapy. Pharm Res-Dord, 26:1407, 2009.
Bulzebruck et al., New Aspects in the Staging of Lung Cancer. Prospective Validation of the International Union against Cancer. Tnm. Classification. Cancer, 70:1102-1110, 1992.
Burke et al., The Structural Basis of Camptothecin Interactions with Human Serum-Albumin—Impact on Drug Stability. J Med Chem, 37:40-46, 1994.
Burke et al., Liposomal Stabilization of Camptothecins Lactone Ring. J Am Chem Soc, 114:8318-8319, 1992.
Cao et al., Alkyl esters of Camptothecin and 9-nitrocamptothecin: Synthesis, in vitro pharmacokinetics, toxicity, and antitumor activity. J Med Chem, 41:31-37, 1998.
Cattel et al., Preparation, characterization and properties of sterically stabilized paclitaxel-containing liposomes. J Control Release, 63:19-30, 2000.
Chang et al., Antiangiogenic Targeting Liposomes Increase Therapeutic Efficacy for Solid Tumors. J Biol Chem, 284:12905, 2009.
Cheetham et al., Supermolecular Nanostructures Formed by Anticancer Drug Assembly, J. Am. Chem. Soc., 35:2907-2910, 2013.
Cho et al., Therapeutic Nanoparticles for Drug Delivery in Cancer. Clin. Cancer Res., 14:1310-1316, 2008.
Colson et al., Biologically Responsive Polymeric Nanoparticles for Drug Delivery, Adv. Mater., 24:3878-3886, 2012.
Conover et al., Camptothecin delivery systems: enhanced efficacy and tumor accumulation of Camptothecin following its conjugation to polyethylene glycol via a glycine linker. Cancer Chemoth Pharm, 42:407, 1998.
Davis et al., Cyclodextrin Based Pharmaceutics: Past, Present and Future, Nat. Rev. Drug Discovery, 3:1023-1035, 2004.
Davis et al., Nanoparticle therapeutics: an emerging treatment modality for cancer, Nat. Rev. Drug Discovery, 1:771-782, 2008.
Dosio et al., Preparation, characterization and properties in vitro and in vivo of a paclitaxel-albumin conjugate., J Control Release, 47:293, 1997.
Elsabahy et al., Design of polymeric nanoparticles for biomedical delivery applications, Chem. Soc. Rev., 11:2545-2561, 2012.
Fassberg et al., A Kinetic and Mechanistic Study of the Hydrolysis of Camptothecin and Some Analogs. J Pharm Sci, 81:676, 1992.
Feng et al., Sequential Functionalization of Janus-Type Dendrimer-Like Poly(ethylene oxide)s with Camptothecin and Folic Acid, J. Polym. Sci. Pol. Chem., 49:2839-2849, 2011.
Fox et al., Soluble Polymer Carriers for the Treatment of Cancer: The Importance of Molecular Architecture. Accounts Chem Res, 42:1141, 2009.
Gao et al., In vivo cancer targeting and imaging with semiconductor quantum dots, Nat. Biotechnol., 22:969-976, 2004.
Geng et al., Hydrolytic degradation of poly(ethylene oxide)-block-polycaprolactone worm micelles. J Am Chem Soc, 127:12780, 2005.
Gibson et al., Paclitaxel-Functionalized Gold Nanoparticles, J. Am. Chem. Soc., 129:11653-11661, 2007.
Gillies et al., Stimuli-responsive supramolecular assemblies of linear-dendritic copolymers, J Am Chem Soc, 126:11936, 2004.
Greenwald et al., 20-O-acylcamptothecin derivatives: Evidence for lactone stabilization, J Org Chem, 65:4601-4606, 2000.
Greenwald, Poly(ethylene glycol) Anticancer Drug delivery systems, Pharmaccutical Sciences, 21:113-121, 2002.
Henne et al., Synthesis and activity of a folate peptide camptothecin prodrug, Bioorg Med Chem Lett, 16:5350-5355, 2006.

(56) References Cited

OTHER PUBLICATIONS

Hertzberg et al., Modification of the Hydroxy Lactone Ring of Camptothecin—Inhibition of Mammalian Topoisomerase-I and Biological-Activity, J Med Chem, 32:715-720, 1989.

Hsiang et al., Camptothecin Induces Protein-Linked DNA Breaks Via Mammalian DNA Topoisomerase-I, J Biol Chem, 260:4873-14878, 1985.

Jaxel et al., Structure-Activity Study of the Actions of Camptothecin Derivatives on Mammalian Topoisomerase-I—Evidence for a Specific Receptor-Site and a Relation to Antitumor-Activity, Cancer Res, 49:1465, 1989.

Ji et al., Carbon nanotubes in cancer diagnosis and therapy, BBA-Rev. Cancer, 1806:29-35, 2010.

Kaminskas et al., Association of Chemotherapeutic Drugs with Dendrimer Nanocarriers: An Assessment of the Merits of Covalent Conjugation Compared to Noncovalent EncapsulationJ. Mol. Pharm., 9:355-373, 2012.

Klein et al., Synthesis and in vivo antitumor activity of poly(L-glutamic acid) conjugates of 20(S)-camptothecin. J Med Chem, 46:190-193, 2003.

Lavergne et al., Homocamptothecin, an E-ring modified camptothecin with enhanced lactone stability, retains topoisomerase I-targeted activity and antitumor properties. Cancer Res 59:2939, 1999.

Lee et al., Polymer-caged lipsomes: A pH-Responsive delivery system with high stability. J Am Chem Soc, 129:15096, 2007.

Lerchen et al., Design and optimization of 20-O-linked camptothecin glycoconjugates as anticancer agents. J Med Chem, 44:4186, 2001.

Li et al., Review Camptothecin: Current Perspectives, Curr. Med. Chem., 13:2021-2039, 2006.

Lim et al., Design, Synthesis, Characterization, and Biological Evaluation of Triazine Dendrimers Bearing Paclitaxel Using Ester and Ester/Disulfide Linkages, Bioconjugate Chem., 20:2154-2161, 2009.

Linderoth et al., Mechanistic Study of the sPLA(2)-Mediated Hydrolysis of a Thio-ester Pro Anticancer Ether Lipid. J Am Chem Soc, 131:12193, 2009.

Longley, et al., 5-Fluorouracil: Mechanisms of Action and Clinical Strategies. Nat. Rev. Cancer, 3:330-338, 2003.

Lundberg, Biologically active camptothecin derivatives for incorporation into liposome bilayers and lipid emulsions, Anti-Cancer Drug Des., 13:453-461, 1998.

Liu et al., Polymer-Based Therapeutics. Macromolecules, 42:3, 2009.

Lutz et al., Modem trends in polymer bioconjugates design. Prog Polym Sci, 33:1, 2008.

Mitra et al., Polymeric conjugates of mono- and bi-cyclic alpha(V)beta(3) binding peptides for tumor targeting. J Control Release, 114:175, 2006.

Maeda et al., Conjugates of Anticancer Agents and Polymers—Advantages of Macromolecular Therapeutics In vivo. Bioconjugate Chem, 3:351, 1992.

Mathijssen et al., Clinical Pharmacokinetics and Metabolism of Irinotecan (CPT-11), Clin. Cancer Res., 7:2182-2194, 2001.

\* cited by examiner (A)..........................................(B)

SEQUENCE LISTING

```
<160> NUMBER OF SEQ ID NOS: 8

<210> SEQ ID NO 1
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Fmoc
<220> FEATURE:
<221> NAME/KEY: MISC_FEATURE
<222> LOCATION: (4)..(4)
<223> OTHER INFORMATION: Camptothecin

<400> SEQUENCE: 1

Lys Phe Lys Lys
1

<210> SEQ ID NO 2
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(2)
<223> OTHER INFORMATION: Xaa is independent of the other, arginyl,
      histidyl, lysyl, aspartyl, glutamyl, seryl, threonyl, cystyl,
      asparagyl, glutaminyl, prolyl, tyrosyl, methionyl, and
      tryptophanyl
<220> FEATURE:
<221> NAME/KEY: MISC_FEATURE
<222> LOCATION: (3)..(4)
<223> OTHER INFORMATION: Xaa is independent of the others, alanyl,
      allosoleucyl, arginyl, asparagyl, aspartyl, cystyl, glutamyl,
      glutaminyl, glycyl, histidyl, isolelucyl, leucyl, lysyl,
      methionyl, phenylalanyl, prolyl, pyroglutamyl, seryl, threonyl,
      tyrosyl, tryptophanyl, or
```

-continued

```
<400> SEQUENCE: 2

Xaa Xaa Xaa Xaa
1

<210> SEQ ID NO 3
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is independent of the other, arginyl,
      histidyl, lysyl, aspartyl, glutamyl, seryl, threonyl, cystyl,
      asparagyl, glutaminyl, prolyl, tyrosyl, methionyl, and
      tryptophanyl
<220> FEATURE:
<221> NAME/KEY: MISC_FEATURE
<222> LOCATION: (2)..(2)
<223> OTHER INFORMATION: Xaa is independent of the others, alanyl,
      allosoleucyl, arginyl, asparagyl, aspartyl, cystyl, glutamyl,
      glutaminyl, glycyl, histidyl, isolelucyl, leucyl, lysyl,
      methionyl, phenylalanyl, prolyl, pyroglutamyl, seryl, threonyl,
      tyrosyl, tryptophanyl, or
<220> FEATURE:
<221> NAME/KEY: MISC_FEATURE
<222> LOCATION: (3)..(3)
<223> OTHER INFORMATION: Xaa is independent of the other, arginyl,
      histidyl, lysyl, aspartyl, glutamyl, seryl, threonyl, cystyl,
      asparagyl, glutaminyl, prolyl, tyrosyl, methionyl, and
      tryptophanyl
<220> FEATURE:
<221> NAME/KEY: MISC_FEATURE
<222> LOCATION: (4)..(4)
<223> OTHER INFORMATION: Xaa is independent of the others, alanyl,
      allosoleucyl, arginyl, asparagyl, aspartyl, cystyl, glutamyl,
      glutaminyl, glycyl, histidyl, isolelucyl, leucyl, lysyl,
      methionyl, phenylalanyl, prolyl, pyroglutamyl, seryl, threonyl,
      tyrosyl, tryptophanyl, or

<400> SEQUENCE: 3

Xaa Xaa Xaa Xaa
1

<210> SEQ ID NO 4
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(2)
<223> OTHER INFORMATION: Xaa is independent of the others, alanyl,
      allosoleucyl, arginyl, asparagyl, aspartyl, cystyl, glutamyl,
      glutaminyl, glycyl, histidyl, isolelucyl, leucyl, lysyl,
      methionyl, phenylalanyl, prolyl, pyroglutamyl, seryl, threonyl,
      tyrosyl, tryptophanyl, or
<220> FEATURE:
<221> NAME/KEY: MISC_FEATURE
<222> LOCATION: (3)..(4)
<223> OTHER INFORMATION: Xaa is independent of the other, arginyl,
      histidyl, lysyl, aspartyl, glutamyl, seryl, threonyl, cystyl,
      asparagyl, glutaminyl, prolyl, tyrosyl, methionyl, and
      tryptophanyl

<400> SEQUENCE: 4

Xaa Xaa Xaa Xaa
1

<210> SEQ ID NO 5
```

```
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is independent of the others, alanyl,
      allosoleucyl, arginyl, asparagyl, aspartyl, cystyl, glutamyl,
      glutaminyl, glycyl, histidyl, isolecucyl, leucyl, lysyl,
      methionyl, phenylalanyl, prolyl, pyroglutamyl, seryl, threonyl,
      tyrosyl, tryptophanyl, or
<220> FEATURE:
<221> NAME/KEY: MISC_FEATURE
<222> LOCATION: (2)..(2)
<223> OTHER INFORMATION: Xaa is independent of the other, arginyl,
      histidyl, lysyl, aspartyl, glutamyl, seryl, threonyl, cystyl,
      asparagyl, glutaminyl, prolyl, tyrosyl, methionyl, and
      tryptophanyl
<220> FEATURE:
<221> NAME/KEY: MISC_FEATURE
<222> LOCATION: (3)..(3)
<223> OTHER INFORMATION: Xaa is independent of the others, alanyl,
      allosoleucyl, arginyl, asparagyl, aspartyl, cystyl, glutamyl,
      glutaminyl, glycyl, histidyl, isolecucyl, leucyl, lysyl,
      methionyl, phenylalanyl, prolyl, pyroglutamyl, seryl, threonyl,
      tyrosyl, tryptophanyl, or
<220> FEATURE:
<221> NAME/KEY: MISC_FEATURE
<222> LOCATION: (4)..(4)
<223> OTHER INFORMATION: Xaa is independent of the other, arginyl,
      histidyl, lysyl, aspartyl, glutamyl, seryl, threonyl, cystyl,
      asparagyl, glutaminyl, prolyl, tyrosyl, methionyl, and
      tryptophanyl

<400> SEQUENCE: 5

Xaa Xaa Xaa Xaa
1

<210> SEQ ID NO 6
<211> LENGTH: 4
<212> TYPE: PRT
<213> ORGANISM: Artificial Sequence
<220> FEATURE:
<223> OTHER INFORMATION: Synthetic Construct

<400> SEQUENCE: 6

Lys Phe Lys Lys
1

<210> SEQ ID NO 7
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (4)..(4)
<223> OTHER INFORMATION: Camptothecin
```

```
<400> SEQUENCE: 7

Lys Phe Lys Lys
1

<210> SEQ ID NO 8
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Camptothecin

<400> SEQUENCE: 8

Lys Phe Lys Lys
1
```

SELF-ASSEMBLY OF THERAPEUTIC AGENT-PEPTIDE NANOSTRUCTURES

CROSS REFERENCE TO RELATED APPLICATIONS

This application claims the benefit of priority to U.S. Provisional Application No. 61/732,655, filed Dec. 3, 2012, which is incorporated by reference herein in its entirety.

ACKNOWLEDGEMENT OF GOVERNMENT SUPPORT

This invention was made with government support under Grant No. CHE-1057884 awarded by The National Science Foundation. The Government has certain rights in this invention.

BACKGROUND

Camptothecin (CPT), originally isolated from the Chinese tree Camptotheca acuminate, possesses potent antitumor properties that emerge from its inhibition of topoisomerase I (Hsiang et al., Camptothecin Induces Protein-Linked DNA Breaks Via Mammalian DNA Topoisomerase-I. *J Biol Chem* 1985, 260, 4873; Lavergne et al., Homocamptothecin, an E-ring modified camptothecin with enhanced lactone stability, retains topoisomerase I-targeted activity and antitumor properties. *Cancer Res* 1999, 59, 2939; Saltz et al., The camptothecins. *Lancet* 2003, 361, 2235). However, CPT exhibits several properties that severely limit its clinical application such as low aqueous solubility, (Lerchen et al., Design and optimization of 20-O-linked camptothecin glycoconjugates as anticancer agents. *J Med Chem* 2001, 44, 4186; Klein et al., Synthesis and in vivo antitumor activity of poly(L-glutamic acid) conjugates of 20(S)-camptothecin. *J Med Chem* 2003, 46, 190; Saltz et al., id.) high levels of protein binding, and rapid inactivation through lactone ring hydrolysis. The insolubility of CPT has severely restricted its clinical application and has led to the development of several water soluble congeners, which are in various phases of clinical trials or in the clinic (Potmesil, Camptothecins—from Bench Research to Hospital Wards. *Cancer Res* 1994, 54, 1431). Camptothecin undergoes a reversible, pH-dependent ring opening reaction between the active lactone (closed E-ring) and inactive carboxylate (open E-ring) form, which has also been shown to be toxic (Greenwald et al., 20-O-acylcamptothecin derivatives: Evidence for lactone stabilization. *J Org Chem* 2000, 65, 4601; Lerchen et al., id). Lactone hydrolysis is also enhanced by the specific binding and sequestration of the carboxylate form to various proteins, such as human serum albumin, in the biological matrix, which shifts the equilibrium further toward the carboxylate form. Thus, the clinical utility of CPT has been severely hindered by the hydrolytic instability of its E-lactone ring in blood serum (Jaxel et al., Structure-Activity Study of the Actions of Camptothecin Derivatives on Mammalian Topoisomerase-I-Evidence for a Specific Receptor-Site and a Relation to Antitumor-Activity. *Cancer Res* 1989, 49, 1465; Hertzberg et al., Modification of the Hydroxy Lactone Ring of Camptothecin—Inhibition of Mammalian Topoisomerase-I and Biological-Activity. *J Med Chem* 1989, 32, 715; Fassberg et al., A Kinetic and Mechanistic Study of the Hydrolysis of Camptothecin and Some Analogs. *J Pharm Sci* 1992, 81, 676; Burke et al., The Structural Basis of Camptothecin Interactions with Human Serum-Albumin—Impact on Drug Stability. *J Med Chem* 1994, 37, 40). Additionally, considerable variability in the oral and intravenous bioavailability of CPT suggests poor cellular and tumor uptake of unmodified CPT drugs (Sinka et al., Tumor-targeted bioconjugate based delivery of camptothecin: design, synthesis and in vitro evaluation. *J Control Release* 2004, 100, 275).

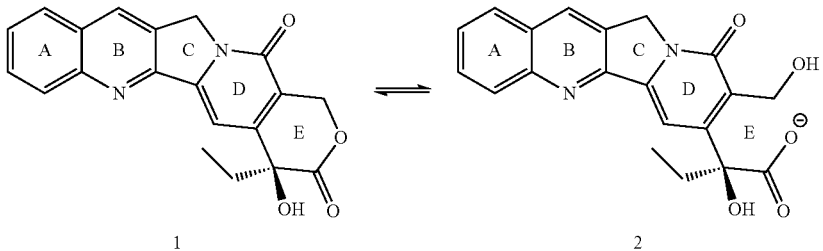

Structure of Camptothecin (CPT) in Lactone (1) and Carboxylate (2) Forms

Appending CPT derivatives to carriers with nanometer dimensions has emerged as a strategy to address many of the limitations of this anticancer drug. Accordingly, nanoscale drug delivery systems (Park et al., Polymeric nanomedicine for cancer therapy. *Frog Polym Sci* 2008, 33, 113; Patil et al., Engineered nanocarriers of doxorubicin: A current update. *Crit Rev Ther Drug* 2008, 25, 1; Fox et al., Soluble Polymer Carriers for the Treatment of Cancer: The Importance of Molecular Architecture. *Accounts Chem Res* 2009, 42, 1141; Riehemann et al., Nanomedicine-Challenge and Perspectives. *Angew Chem Int Edit* 2009, 48, 872; Subramani et al., Targeting Nanoparticles as Drug Delivery Systems for Cancer Treatment. *Curr Nanosci* 2009, 5, 135; Zhang et al., Polymeric Core-Shell Assemblies Mediated by Host-Guest Interactions: Versatile Nanocarriers for Drug Delivery. *Angew Chem Int Edit* 2009, 48, 964) based on liposomes (Lee et al., Polymer-caged lipsomes: A pH-Responsive delivery system with high stability. *J Am Chem Soc* 2007, 129, 15096; Wu et al., AEI 26-Interfacial nanomedicine: Remotely triggered liposomal release by near-infrared light absorption via hollow gold nanoshells. *Abstr Pap Am Chem S* 2008, 236; Chang et al., Antiangiogenic Targeting Liposomes Increase Therapeutic Efficacy for Solid Tumors. *J Biol Chem* 2009, 284, 12905; Linderoth et al., Mechanistic Study of the sPLA(2)-Mediated Hydrolysis of a Thio-ester Pro Anticancer Ether Lipid. *J Am Chem Soc* 2009, 131, 12193; Volodkin et al., Near-IR Remote Release from Assemblies of Liposomes and Nanoparticles. *Angew Chem*

Int Edit 2009, 48, 1807), water soluble polymers (Mitra et al., Polymeric conjugates of mono- and bi-cyclic alpha(V) beta(3) binding peptides for tumor targeting. *J Control Release* 2006, 114, 175; Satchi-Fainaro et al., Polymer therapeutics for cancer: Current status and future challenges. *Adv Polym Sci* 2006, 193, 1; Lutz et al., Modern trends in polymer bioconjugates design. *Prog Polym Sci* 2008, 33, 1; Borgman et al., Targetable HPMA Copolymer-Aminohexylgeldanamycin Conjugates for Prostate Cancer Therapy. *Pharm Res-Dord* 2009, 26, 1407; Liu et al., Polymer-Based Therapeutics. *Macromolecules* 2009, 42, 3), dendrimers (Gillies et al., Stimuli-responsive supramolecular assemblies of linear-dendritic copolymers. *J Am Chem Soc* 2004, 126, 11936; Ambade et al., Dendrimeric micelles for controlled drug release and targeted delivery. *Mol Pharmaceut* 2005, 2, 264), inorganic nanoparticles, and vesicles (Geng et al., Hydrolytic degradation of poly(ethylene oxide)-block-polycaprolactone worm micelles. *J Am Chem Soc* 2005, 127, 12780; Soussan et al., Drug Delivery by Soft Matter: Matrix and Vesicular Carriers. *Angew Chem Int Edit* 2009, 48, 274), inter alia, have been extensively studied. Nanoscale drug carriers have been exploited to improve water solubility, drug stability (Burke et al., Liposomal Stabilization of Camptothecins Lactone Ring. *J Am Chem Soc* 1992, 114, 8318; Greenwald et al., Drug delivery systems 0.2. Camptothecin 20-O-poly(ethylene glycol)ester transport forms. *J Med Chem* 1996, 39, 1938), prolong circulation times (Watanabe et al., Preparation of camptothecin-loaded polymeric micelles and evaluation of their incorporation and circulation stability. *Int J Pharm* 2006, 308, 183), and facilitate passive accumulation in tumors via the enhanced permeability and retention (EPR) effect (Maeda et al., Conjugates of Anticancer Agents and Polymers—Advantages of Macromolecular Therapeutics In vivo. *Bioconjugate Chem* 1992, 3, 351; Yu et al., Antitumor activity of poly(ethylene glycol)-Camptothecin conjugate: The inhibition of tumor growth in vivo. *J Control Release* 2005, 110, 90). However, the mass of many of these systems is dominated by the large size of the inert carrier, compared with that of the active drug, thus requiring large doses to be administered. For clinical applications, repeated administrations of high doses of drug carriers have the potential for systemic toxicity as well as the extra burden for patients to excrete the carriers (Shen et al., Prodrugs Forming High Drug Loading Multifunctional Nanocapsules for Intracellular Cancer Drug Delivery. *J Am Chem Soc* 2010, 132, 4259). Ideally, such nanomedicines would be primarily composed of drug, and otherwise nontoxic to the patient.

Unfortunately, the difficulties with Camptothecin are shared by many other hydrophobic and/or unstable drugs. Thus, what are needed are new compositions that allow greater stability and delivery of such drugs, while maintaining high loading and concentrations of the drug in the composition. Such a platform is disclosed herein and exemplified for various drugs.

SUMMARY

In accordance with the purposes of the disclosed materials, compounds, compositions, articles, devices, and methods, as embodied and broadly described herein, the disclosed subject matter relates to compositions and methods of making and using the compositions. In a specific aspect, disclosed are nanotubes that comprise a wall, wherein the wall is formed from a congjuate. The conjugates comprise a hydrophobic drug linked to a hydrophilic amino acid or peptide and can self assemble into the nanotube wall. Methods for forming the conjugates and nanotubes and using them to stabilize and deliver the drugs are also disclosed.

Additional advantages of the disclosed subject matter will be set forth in part in the description that follows, and in part will be obvious from the description, or can be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE FIGURES

The accompanying Figures, which are incorporated in and constitute a part of this specification, illustrate several aspects of the invention and together with the description serve to explain the principles of the invention.

Inset: zoom-in image of individual sheet rolled into tube. TEM images were obtained on a carbon-coated copper grid with a negative stain.

Figure 8:
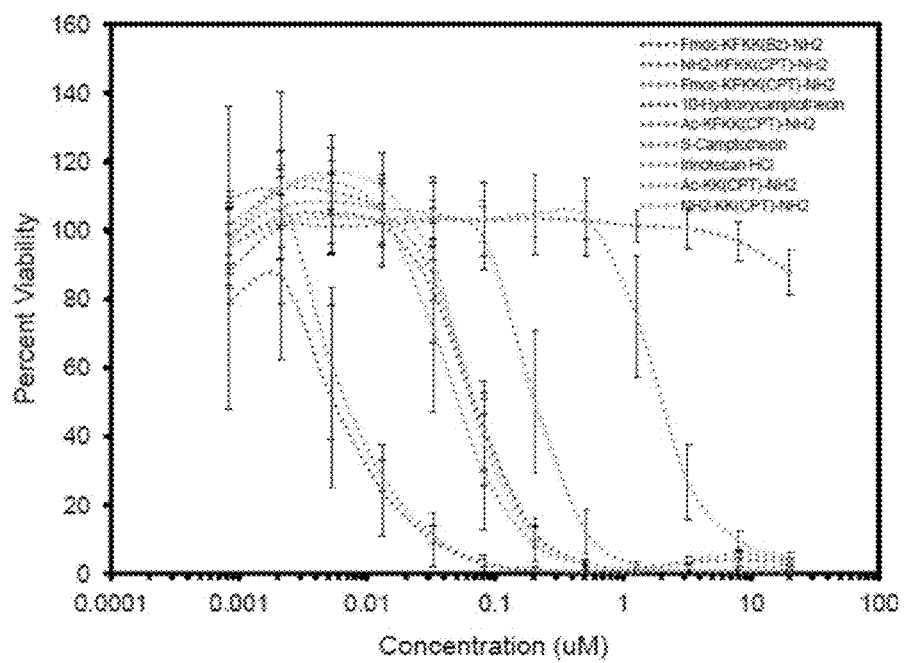

FIG. 8. is a graph from an In vitro cell assay for camptothecins. Error bars represent standard deviation.

Figure 9:
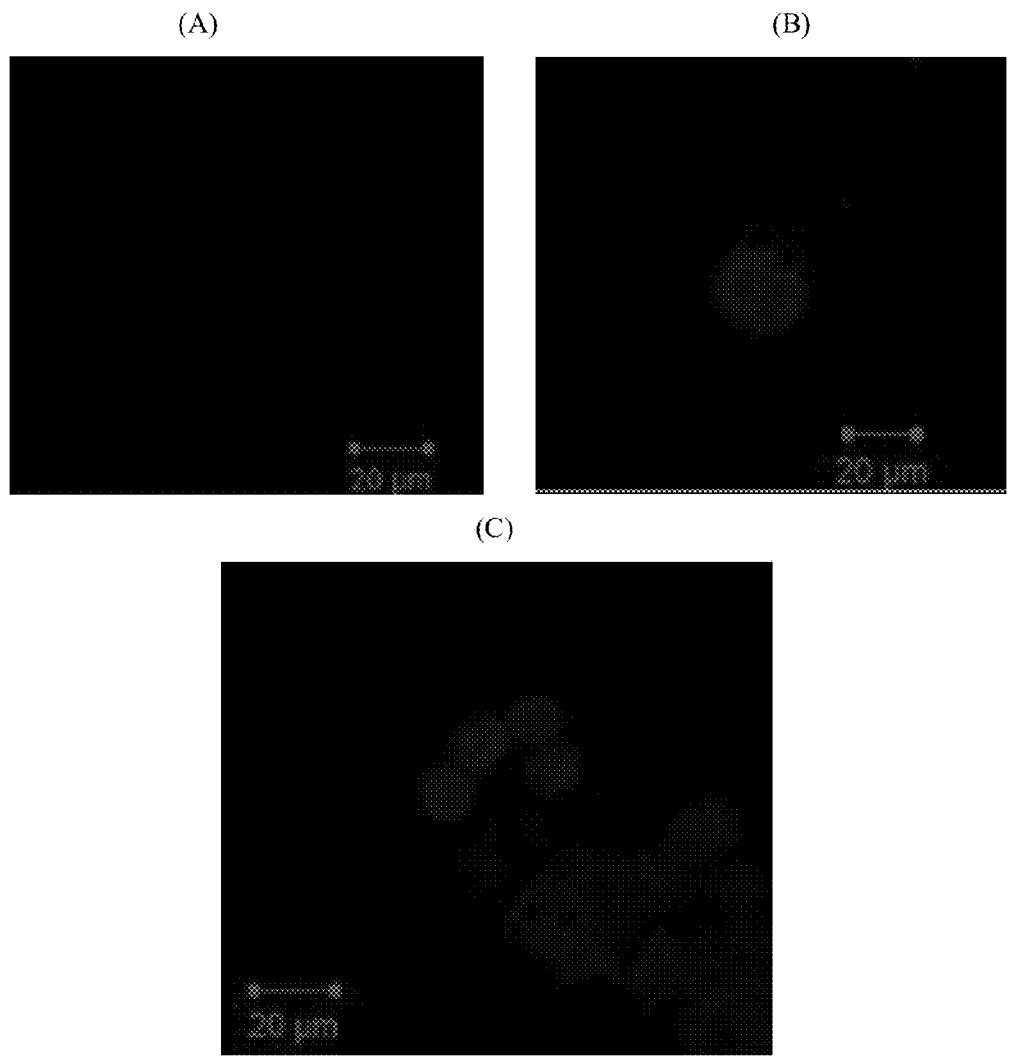

FIG. 9 is a group of confocal microscopy images (fluorescence) of HT-29 cells. (A) Control cells, unexposed to camptothecin drug; the absence of drug gives no fluorescent signal. (B) Cells exposed to Fmoc-KFKK(CPT)-NH$_2$ (SEQ ID NO:1). (C) Cells exposed to Irinotecan HCl.

Figure 10:
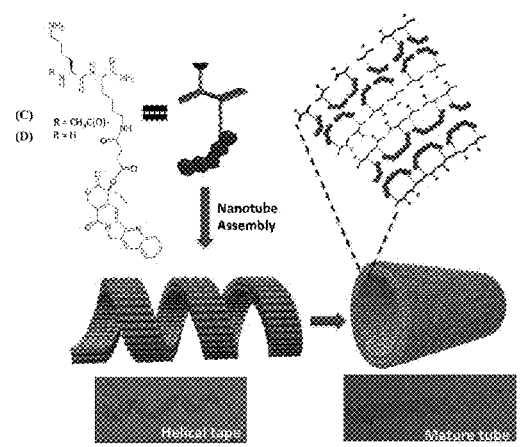

FIG. 10 is a schematic showing the self assembly of two conjugates as disclosed herein into a helical tape and nanotube structure.

Figure 11:
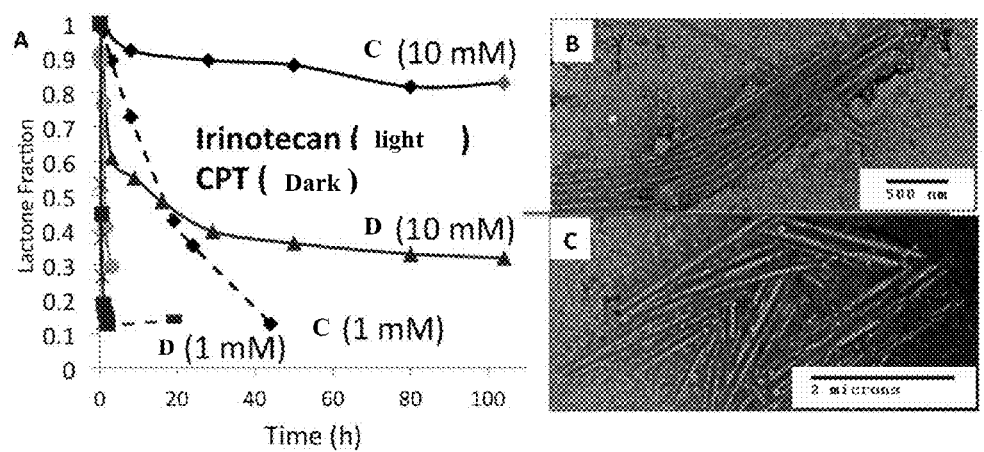

FIG. 11 (A) is a graph showing lactone stability of CPT-dipeptides Ac-KK(CPT)-NH$_2$ (C), and NH$_2$—KK(CPT)-NH$_2$ (D) in human serum (HS) at 37° C. (pH 7.4) at 1 and 10 mM, as monitored by HPLC. The stability of CPT and Irinotecan in HS is shown in light and dark, respectively. TEM images of (B) C and (C) D incubated in HS for 24 hours. Samples were prepared at 10 mM in PBS and subsequently diluted to 1 mM in HS after 24 h.

Figure 12:
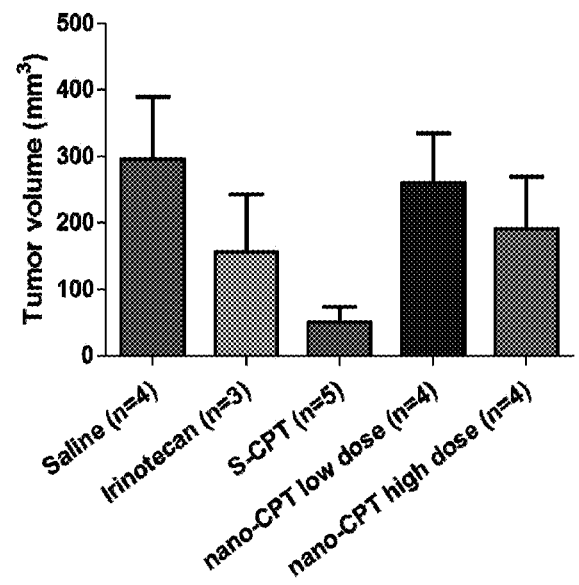

FIG. 12 is a graph showing the results of a Lewis Lung Carcinoma assay.

Figure 13:
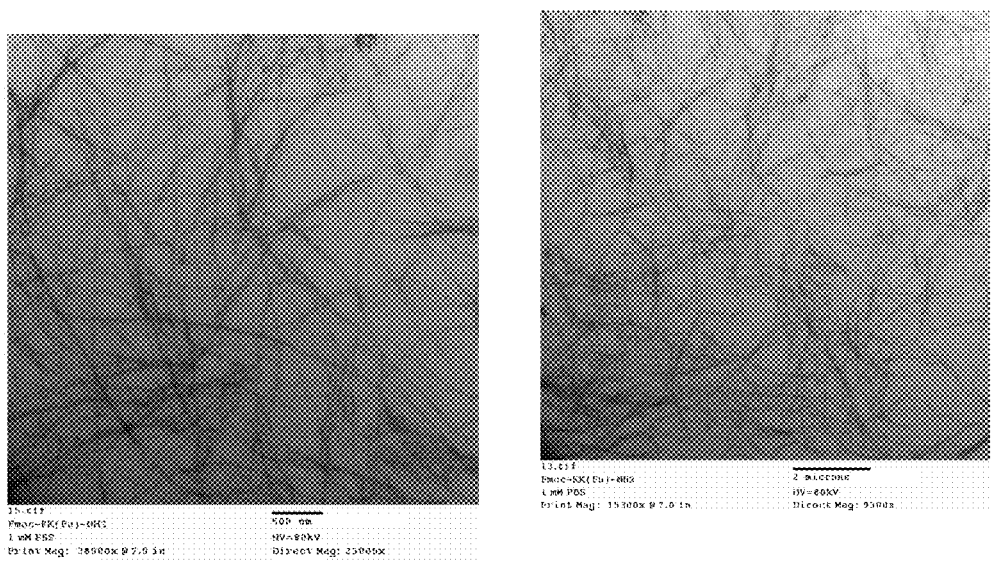

FIG. 13 is a pair of TEM images from Fmoc-KK-(5-Fu)-NH2 conjugates in 1 mM PCB at different magnifications.

DETAILED DESCRIPTION

The compounds, compositions, articles, devices, and methods described herein can be understood more readily by reference to the following detailed description of specific aspects of the disclosed subject matter and the Examples and Figures.

Before the present compounds, compositions, articles, devices, and methods are disclosed and described it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

As used in the description and the appended claims, the singular forms "a," "an," and "the" include plural referents unless the context clearly dictates otherwise. Thus, for example, reference to "a composition" includes mixtures of two or more such compositions, reference to "the compound" includes mixtures of two or more such compounds, and the like.

"Optional" or "optionally" means that the subsequently described event or circumstance can or cannot occur, and that the description includes instances where the event or circumstance occurs and instances where it does not.

When ranges of values are disclosed, and the notation "from $n_1$ ... to $n_2$" is used, where $n_1$ and $n_2$ are the numbers, then unless otherwise specified, this notation is intended to include the numbers themselves and the range between them. This range can be integral or continuous between and including the end values. By way of example, the range "from 2 to 6 carbons" is intended to include two, three, four, five, and six carbons, since carbons come in integer units. Compare, by way of example, the range "from 1 to 3 µM (micromolar)," which is intended to include 1 µM, 3 µM, and everything in between to any number of significant figures (e.g., 1.255 µM, 2.1 µM, 2.9999 µM, etc.).

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

Chemical Definitions

As used herein, the term "amphiphilic" means the ability to dissolve in both water and lipids/apolar environments. Typically, an amphiphilic compound comprises a hydrophilic portion and a hydrophobic portion. "Hydrophobic" designates a preference for apolar environments (e.g., a hydrophobic substance or moiety is more readily dissolved in or wetted by non-polar solvents, such as hydrocarbons, than by water). As used herein, the term "hydrophilic" means the ability to dissolve in water.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

When substituted, the substituents of a substituted group can include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen or deuterium, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, $N_3$, SH, $SCH_3$, $C(O)CH_3$, $CO_2CH_3$, $CO_2H$, pyridinyl, thiophene, furanyl, lower carbamate, and lower urea. Two substituents can be joined together to form a fused five-, six-, or seven-membered carbocyclic or heterocyclic ring consisting of zero to three heteroatoms, for example forming methylenedioxy or ethylenedioxy. An optionally substituted group can be unsubstituted (e.g., —$CH_2CH_3$), fully substituted (e.g., —$CF_2CF_3$), monosubstituted (e.g., —$CH_2CH_2F$) or substituted at a level anywhere in-between fully substituted and monosubstituted (e.g., —$CH_2CF_3$). Where substituents are recited without qualification as to substitution, both substituted and unsubstituted forms are encompassed. Where a substituent is qualified as "substituted," the substituted form is specifically intended.

"$Z^1$," "$Z^2$," "$Z^3$," and "$Z^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" as used herein refers to a non-aromatic hydrocarbon group and includes branched and unbranched, alkyl, alkenyl, or alkynyl groups.

The term "alkyl" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "alkoxy" as used herein is an alkyl group bound through a single, terminal ether linkage; that is, an "alkoxy" group can be defined as —$OZ^1$ where $Z^1$ is alkyl as defined above.

The term "alkenyl" as used herein is a hydrocarbon group of from 2 to 24 carbon atoms with a structural formula containing at least one carbon-carbon double bond. Asymmetric structures such as $(Z^1Z^2)C=C(Z^3Z^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "alkynyl" as used herein is a hydrocarbon group of 2 to 24 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "aryl" as used herein is a group that contains any carbon-based aromatic group including, but not limited to, benzene, naphthalene, phenyl, biphenyl, phenoxybenzene, and the like. The term "heteroaryl" is defined as a group that contains an aromatic group that has at least one heteroatom incorporated within the ring of the aromatic group. Examples of heteroatoms include, but are not limited to, nitrogen, oxygen, sulfur, and phosphorus. The term "non-heteroaryl," which is included in the term "aryl," defines a group that contains an aromatic group that does not contain a heteroatom. The aryl or heteroaryl group can be substituted or unsubstituted. The aryl or heteroaryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one double bond, i.e., C=C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above, and is included within the meaning of the term "cycloalkenyl," where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "aldehyde" as used herein is represented by the formula —C(O)H. Throughout this specification "C(O)" or "CO" is a short hand notation for C═O, which is also referred to herein as a "carbonyl."

The terms "amine" or "amino" as used herein are represented by the formula —NZ$^1$Z$^2$, where Z$^1$ and Z$^2$ can each be substitution group as described herein, such as hydrogen, an alkyl, halogenated alkyl, alkenyl, alkynyl, aryl, heteroaryl, cycloalkyl, cycloalkenyl, heterocycloalkyl, or heterocycloalkenyl group described above. "Amido" is —C(O)NZ$^1$Z$^2$.

The term "carboxylic acid" as used herein is represented by the formula —C(O)OH. A "carboxylate" or "carboxyl" group as used herein is represented by the formula —C(O)O$^-$.

The term "ester" as used herein is represented by the formula —OC(O)Z$^1$ or —C(O)OZ$^1$, where Z$^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula Z$^1$OZ$^2$, where Z$^1$ and Z$^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula Z$^1$C(O)Z$^2$, where Z$^1$ and Z$^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" or "halogen" as used herein refers to the fluorine, chlorine, bromine, and iodine.

The term "hydroxyl" as used herein is represented by the formula —OH.

The term "lower," as used herein, alone or in a combination, where not otherwise specifically defined, means containing from 1 to and including 6 carbon atoms.

The term "lower alkyl," as used herein, alone or in a combination, means $C_1$-$C_6$ straight or branched chain alkyl. The term "lower alkenyl" means $C_2$-$C_6$ straight or branched chain alkenyl. The term "lower alkynyl" means $C_2$-$C_6$ straight or branched chain alkynyl.

The term "lower aryl," as used herein, alone or in combination, means phenyl or naphthyl, either of which can be optionally substituted as provided.

The term "lower heteroaryl," as used herein, alone or in combination, means either 1) monocyclic heteroaryl comprising five or six ring members, of which between one and four said members can be heteroatoms chosen from O, S, and N, or 2) bicyclic heteroaryl, wherein each of the fused rings comprises five or six ring members, comprising between them one to four heteroatoms chosen from O, S, and N.

The term "lower cycloalkyl," as used herein, alone or in combination, means a monocyclic cycloalkyl having between three and six ring members. Lower cycloalkyls can be unsaturated. Examples of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between three and six ring members, of which between one and four can be heteroatoms chosen from O, S, and N. Examples of lower heterocycloalkyls include pyrrolidinyl, imidazolidinyl, pyrazolidinyl, piperidinyl, piperazinyl, and morpholinyl. Lower heterocycloalkyls can be unsaturated.

The term "lower carboxyl," as used herein, alone or in combination, means —C(O)R, wherein R is chosen from hydrogen, lower alkyl, cycloalkyl, cycloheterolkyl, and lower heteroalkyl, any of which can be optionally substituted with hydroxyl, (O), and halogen.

The term "lower amino," as used herein, alone or in combination, refers to —NRR', wherein R and R' are independently chosen from hydrogen, lower alkyl, and lower heteroalkyl, any of which can be optionally substituted. Additionally, the R and R' of a lower amino group can combine to form a five- or six-membered heterocycloalkyl, either of which can be optionally substituted.

The term "nitro" as used herein is represented by the formula —NO$_2$.

The term "nanotube" is used herein in a general sence to refer to an elongated nanostructure. This term is meant to include nanobars, nanowhiskers, helixes, nanospheres, and the like. In some examples, the nanotube is not a β-sheet.

The term "silyl" as used herein is represented by the formula —SiZ$^1$Z$^2$Z$^3$, where Z$^1$, Z$^2$, and Z$^3$ can be, independently, hydrogen, alkyl, halogenated alkyl, alkoxy, alkenyl, alkynyl, aryl, heteroaryl, cycloalkyl, cycloalkenyl, heterocycloalkyl, or heterocycloalkenyl group described above.

The term "sulfonyl" is used herein to refer to the sulfo-oxo group represented by the formula —S(O)$_2$Z$^1$, where Z$^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula —S(O)$_2$NH—.

The term "thiol" as used herein is represented by the formula —SH.

The term "thio" as used herein is represented by the formula —S—.

"R$^1$," "R$^2$," "R$^3$," "R$^n$," etc., where n is some integer, as used herein can, independently, possess one or more of the groups listed above. For example, if R$^1$ is a straight chain alkyl group, one of the hydrogen atoms of the alkyl group can optionally be substituted with a hydroxyl group, an alkoxy group, an amine group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

The term "disease" as used herein is intended to be generally synonymous, and is used interchangeably with, the terms "disorder," "syndrome," and "condition" (as in medical condition), in that all reflect an abnormal condition of the human or animal body or of one or more of its parts that impairs normal functioning, is typically manifested by distinguishing signs and symptoms, and/or causes the human or animal to have a reduced duration or quality of life.

The term "individual" (and, equivalently, "subject") means all mammals including humans. Examples of individuals include humans, cows, dogs, cats, goats, sheep, pigs, and rabbits. Preferably, the individual is a human.

The term "peptide" as used herein refers to short polymers formed from the linking, in a defined order, of α-amino acids. The link between one amino acid residue and the next is known as an amide bond or a peptide bond. Proteins are polypeptide molecules. The distinction is that peptides are short and polypeptides/proteins are long. There are several different conventions to determine these. Peptide chains that are short enough to be made synthetically from the constituent amino acids are called peptides, rather than proteins, with one dividing line at about 50 amino acids in length.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

By "reduce" or other forms of the word, such as "reducing" or "reduction," is meant lowering of an event or characteristic (e.g., tumor growth). It is understood that this is typically in relation to some standard or expected value, in other words it is relative, but that it is not always necessary for the standard or relative value to be referred to. For example, "reduces tumor growth" means reducing the rate of growth of a tumor relative to a standard or a control.

By "treat" or other forms of the word, such as "treated" or "treatment," is meant to administer a composition or to perform a method in order to reduce, prevent, inhibit, or eliminate a particular characteristic or event (e.g., tumor growth or survival). The term "control" is used synonymously with the term "treat."

As used herein, the terms "treating" and "treatment" refer to delaying the onset of, retarding or reversing the progress of, or alleviating or preventing either the disease or condition to which the term applies, or one or more symptoms of such disease or condition.

Reference will now be made in detail to specific aspects of the disclosed materials, compounds, compositions, articles, and methods, examples of which are illustrated in the accompanying Examples and Figures.

Nanotubes

Disclosed herein are conjugates that comprise a hydrophobic drug linked via a linker moiety to a protected or unprotected peptide or single amino acid. The conjugates can self-assemble into nanotubes so that the walls of the nanotubes are characterized by a hydrophilic domain comprising the peptide component of the conjugate and a hydrophobic domain comprising the hydrophobic drug component. By sequestering the hydrophobic drug within the hydrophilic domain in of the nanotube walls, the drug can be protected from water and proteins, and thereby reduce the rate of degradation and/or elimination.

Thus, disclosed herein is a nanotube having a wall, wherein the wall comprises a hydrophobic domain and a hydrophilic domain, and wherein the hydrophobic domain comprises a hydrophobic drug and the hydrophilic domain comprises an amino acid or peptide. The general structure of a nanotube wall as disclosed herein can be shown as follows:

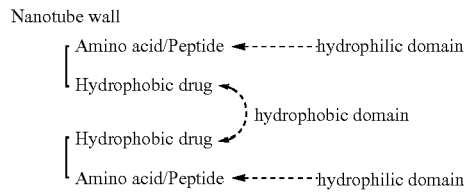

In this wall schematic there are two conjugates shown, each comprising an amino acid or peptide linked to a hydrophobic drug. The conjugates are thus amphiphilic with a hydrophilic portion comprising the amino acid or peptide and a hydrophobic portion comprising the drug. In the simplest sense, two conjugates assemble such that the hydrophobic drug portion of each conjugate associate together and create the internal, hydrophobic domain of the wall, and the amino acid or peptide portion of each conjugate is directed outward and create the hydrophilic domain of the wall. This arrangement is repeated linearly many times over to create the wall of the disclosed nanotube. It is also contemplated that the disclosed nanotubes can be single walled as shown above, or double-walled where one wall is on top of the other (see e.g., FIG. 10). It is also contemplated that the disclosed nanotubes can have more than two walls.

In the disclosed nanotube and conjugate, the hydrophobic drug is a primary component. This means the "loading" or amount of drug in relation to the other components in the nanotube, and thus individual conjugate, is high. This arrangement allows delivery of significant amounts of drug. Thus, in the disclosed nanotubes, the amount of hydrophobic drug is at least about 50 wt. % of the nanotube, for example, the amount of hydrophobic drug is at least about 55, 60, 65, 70, 75, 80, 85, 90, or 95 wt % of the nanotube.

The disclosed nanotube can be defined by its aspect ratio, which is the length of the nanotube divided by the width of the nanotube. The disclosed nanotube can have an aspect ratio of at least about 5; for example, the nanotube can have an aspect ratio of at least about 10, at least about 15, at least about 20, or at least about 25. In some examples, the disclosed nanotube can have an aspect ratio that is about 25 or less; for example, the nanotube can have an aspect ratio of about 20 or less, about 15 or less, about 10 or less, or about 5 or less). The disclosed nanotube can have an aspect ratio ranging from any of the minimum values described above to any of the maximum values described above. For example, the nanotube can have an aspect ratio ranging from about 5 to about 25 (e.g., from at least about 10 to about 20, from about 15 to about 25, from about 10 to about 15, or from about 20 to about 25).

In certain examples, the disclosed nanotube can have a length ranging from about 1 nm to about 500 nm. In specific examples, the disclosed nanotube can have a length ranging from about 1 nm to about 400 nm, from about 1 nm to about 300 nm, from about 1 nm to about 200 nm, from about 1 nm to about 100 nm, from about 100 nm to about 500 nm, from about 100 nm to about 400 nm, from about 100 nm to about 300 nm, from about 100 nm to about 200 nm, from about 200 nm to about 500 nm, from about 200 nm to about 400 nm, from about 200 nm to about 300 nm, from about 300 nm to about 500 nm, from about 300 nm to about 400 nm, or from about 400 nm to about 500 nm. In other examples, the nanotube can have a length of greater than about 500 nm. For examples, the nanotube can have a length ranging from about 500 to about 5 µm, from about 1 µm to about 4 µm, from about 1 µm to about 3 µm, from about 1 to about 2 µm, from about 2 µm to about 5 µm, from about 2 µm to about 4 µm, from about 2 µm to about 3 µm, from about 3 µm to about 5 µm, from about 3 µm to about 4 µm, or from about 4 µm to about 5 µm. It is also contemplated that the disclosed nanotube can have a length of greater than 5 µm.

The surface charge of the disclosed nanotube can influence the stability and movement of the nanotube in tissue. The disclosed nanotube can have a negative Zeta potential, which enhances cell penetration but lowers in vivo stability and mobility. It has been found that near-zero Zeta potentials are preferred, though positive Zeta potential can also be used. For example, the disclosed nanotube can have a Zeta potential of from about −50 mV to about +50 mV, from about −40 mV to about +40 mV, from about −30 mV to about +30 mV, from about −20 mV to about +20 mV, from about −10 mV to about +10 mV, from about −5 mV to about +5 mV, from about −1 mV to about +1 mV. In a preferred example, the disclosed nanotube can have a Zeta potential of about 0 mV.

Conjugates

As mentioned herein, the disclosed nanotube can have one or more walls, each made from conjugates that contain a hydrophobic drug linked to an amino acid or peptide. Thus, in another aspect, disclosed herein is such a conjugate, which can be represented by Formula I.

D-L-AA          (I)

Where D is the hydrophobic drug, L is a linker moiety, and AA is an amino acid residue of a single amino acid or a peptide.

Hydrophobic Drug

The hydrophobic drug can be any drug that is poorly soluble in water, i.e., having a water solubility less than about 10 mg/mL (e.g., less than 1 mg/mL, less than 0.1 mg/mL, or less than 0.01 mg/mL).

Suitable examples of hydrophobic drugs include, but are not limited to, ROCK inhibitors, SYK-specific inhibitors, JAK-specific inhibitors, SYK/JAK or Multi-Kinase inhibitors, MTORs, STAT3 inhibitors, VEGFR/PDGFR inhibitors, c-Met inhibitors, ALK inhibitors, mTOR inhibitors, PI3K5 inhibitors, PBK/mTOR inhibitors, p38/MAPK inhibitors, antibiotics, antivirals, antifungals, antiparsitic agents, blood pressure lowering agents, cancer drugs, immunosuppressants, psychiatric medications, dermatologic drugs, lipid lowering agents, anti-depressants, anti-diabetics, anti-epileptics, anti-gout agents, anti-hypertensive agents, anti-malarials, antimigraine agents, anti-muscarinic agents, anti-thyroid gents, anxiolytic, sedatives, hypnotics, neuroleptics, β-blockers, cardiac inotropic agents, diuretics, anti-parkinsonian agents, gastro-intestinal agents, histamine H-receptor antagonists, anti-anginal agents, opioid analgesics, sex hormones, and stimulants.

In certain examples, the hydrophobic drug is a steroid. Steroids include for example, fluticasone, hydrocortisone, hydrocortisone acetate, cortisone acetate, tixocortol pivalate, prednisolone, methylprednisolone, prednisone, triamcinolone acetonide, triamcinolone alcohol, mometasone, amcinonide, budesonide, desonide, fluocinonide, fluocinolone, fluocinolone acetonide, flunisolide, fluorometholone, clobetasol propionate, loteprednol, medrysone, rimexolone, difluprednate, halcinonide, beclomethasone, betamethasone, betamethasone sodium phosphate, Ciclesonide, dexamethasone, dexamethasone sodium phosphate, dexamethasone acetate, fluocortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate, fluprednidene acetate, prednisolone acetate, prednisolone sodium phosphate, fluorometholone, fluorometholone acetate, loteprednol etabonate, and betamethasone phosphate, including the esters and pharmaceutically acceptable salts thereof.

In certain examples, the hydrophobic drug is a nonsteroidal anti-inflammatory drugs NSAID. Suitable NSAIDs can be, for example, bromfenac, diclofenac sodium, flurbiprofen, ketorolac tromethamine, mapracorat, naproxen, oxaprozin, ibuprofen, and nepafenac, including the esters and pharmaceutically acceptable salts thereof.

In still other examples, the hydrophobic drug can be besifloxacin, DE-110 (Santen Inc.), rebamipide, androgens (DHEA, testosterone, analogs, & derivatives having poor water solubility), estrogens (poorly water soluble compounds that are derivatives of estradiol, estriol, and estrone; e.g., estradiol, levonorgesterol, analogs, isomers or derivatives thereof), progesterone and progestins ($1^{st}$ through $4^{th}$ generation) with poor water solubility (e.g., norethindrone, analogs, and derivatives thereof, medroxyprogesterone, or tagaproget), and pregnenolone. Examples of progestins in various generations include: first generation (estrane) such as norethindrone, norethynodrel, norethindrone acetate, and ethynodiol diacetate; second generation (gonane) such as levonorgestrel, norethisterone, and norgestrel; third generation (gonane) such as desogestrel, gestodene, norgestimate, and drospirenone; and fourth generation such as dienogest, drospirenone, nestorone, nomegestrol acetate and trimegestone.

Other examples of hydrophobic drugs include 10-alkoxy-9-nitrocamptothecin; 17b-estradiol; 3'-azido-3'-deoxythymidine palmitate; 5-amino levulinic acid; ABT-963; aceclofenac; aclacinomycin A; albendazole; alkannin/shikonin; all-trans retinoic acid; alpha-tocopheryl acetate; AMG 517; amprenavir; aprepitant; artemisinin; azadirachtin; baicalein; benzimidazole derivatives; benzoporphyrin; benzopyrimidine derivatives; bicalutamide; BMS-232632; BMS-488043; bromazepam; bropirimine; cabamezapine; candesartan cilexetil; carbamazepine; carbendazim; carvedilol; cefditoren; cefotiam; cefpodoxime proxetil; Cefuroxime axetil; Celecoxib; Ceramide; Cilostazol; Clobetasol propionate; Clotrimazole; Coenzyme Q10; Curcumin; Cycicoporine; Danazol; Dapsone; Dexibuprofen; Diazepam; Dipyridamole; docetaxel; Doxorubicin; Doxorubicin; Econazole; ER-34122; Esomeprazole; Etoricoxib; Etravirine;

Everolimus; Exemestane; Felodipine; Fenofibrate; flurbiprofen; Flutamide; Furosemide; gamma-oryzanol; Glibenclamide; Gliclazide; Gonadorelin; Griseofulvin; Hesperetin; HO-221; Indomethacin; Insulin; Isoniazid; Isotretinoin; Itraconazole; Ketoprofen; LAB687; Limaprost; Liponavir; Loperamide; Mebendazole; Megestrol; Meloxicam; MFB-1041; Mifepristone; MK-0869; MTP-PE; Nabilone; Naringenin; Nicotine; Nilvadipine; Nimesulide; Nimodipine; Nitrendipine; Nitroglycerin; NNC-25-0926; Nobiletin; Octafluoropropane; Oridonin; Oxazepam; Oxcarbazepine; Oxybenzone; Paclitaxel; Paliperidone palmitate; Penciclovir; PG301029; PGE2; Phenytoin; Piroxicam; Podophyllotoxin; Porcine pancreatic lipase and colipase; Probucol; Pyrazinamide; Quercetin; Raloxifene; Resveratrol; Rhein; Rifampicin; Ritonavir; Rosuvastatin; Saquinavir; Silymarin; Sirolimus; Spironolactone; Stavudine; Sulfisoxazole; Tacrolimus; Tadalafil; Tanshinone; Tea polyphenol; Theophylline; Tiaprofenic acid; Tipranavir; Tolbutamide; Tolterodine tartrate; Tranilast; Tretinoin; Triamcinolone acetonide; Triptolide; Troglitazone; Valacyclovir; Verapamil; Vincristine; Vinorelbin-bitartrate; Vinpocetine; Vitamin-E; Warfarin; and XK469.

More examples of suitable hydrophobic drugs include, e.g., amphotericin B, gentamicin and other aminoglycoside antibiotics, ceftriaxone and other cephalosporins, tetracyclines, cyclosporin A, aloxiprin, auranofin, azapropazone, benorylate, diflunisal, etodolac, fenbufen, fenoprofen calcium, meclofenamic acid, mefanamic acid, nabumetone, oxyphenbutazone, phenylbutazone, sulindac, benznidazole, clioquinol, decoquinate, diiodohydroxyquinoline, diloxanide furoate, dinitolmide, furzolidone, metronidazole, nimorazole, nitrofurazone, ornidazole, and tinidazoie.

The hydrophobic drugs suitable for the methods of the invention can also be FDA-approved drugs with cLogP of five or more, such as the following: 2-(4-hydroxy-3,5-diiodobenzyl)cyclohexanecarboxylic Alpha-carotene; Alpha-cyclohexyl-4-hydroxy-3,5-3,3',4',5-tetrachloro salicylanilide diiodohydrocinnamic acid; 4,6-bis(1-methylpentyl)resorcinol Vitamin E; 4,6-dichloro-2-hexylresorcinol Vitamin E acetate; Acitretin Alverine, Alverine Citrate; Adapalene Amiodarone; Alpha-butyl-4-hydroxy-3,5-diiodohydrocinnamic acid Astemizole Atiprimod dihydrochloride Chlorophyll, chlorophyll unk; Atorvastatin, atorvastatin calcium Chlorotrianisene; Benzestrol Chlorprothixene; Bepridil, bepridil hydrochloride Cholecalciferol Beta-carotene Cholesterol; Bexarotene Choline iodide sebacate; Bithionol Cinacalcet; Bitolterol, bitolterol mesylate Cinnarizine; Clindamycin palmitate, clindamycin; Bromthymol blue palmitate hydrochloride; Buclizine, buclizine hydrochloride Clofazimine; Bunamiodyl sodium Cloflucarban; Clomiphene, enclomiphene, Butenafine, butenafine hydrochloride zuclomiphene, clomiphene citrate; Butoconazole, butoconazole nitrate Clotrimazole; Calcifediol Colfosceril palmitate; Calcium oleate Conivaptan; Calcium stearate Cyverine hydrochloride, cyverine; Desoxycorticosterone trimethylacetate, Candesartan cilexetil desoxycorticosterone pivalate; Captodiame, captodiame hydrochloride Dextromethorphan polistirex; Cetyl alcohol Dichlorodiphenylmethane; Chaulmoogric acid Diethylstilbestrol; Chloramphenicol palmitate Diethylstilbestrol dipalmitate Chlorophenothane Diethylstilbestrol dipropionate Dimestrol Ethylamine oleate; Dimyristoyl lecithin, Etretinate; Diphenoxylate, atropine sulfate, diphenoxylate hydrochloride Fenofibrate; Dipipanone, dipipanone hydrochloride Fenretinide; Docosanol Flunarizine, flunarizine hydrochloride; Docusate sodium Fluphenazine decanoate; Domine Fluphenazine enanthate; Doxercalciferol Fosinopril, fosinopril sodium; Promo stanolone propionate Fulvestrant Dronabinol Gamolenic acid, gammalinolenic acid; Glyceryl stearate, glyceryl; Dutasteride monostearate; Econazole, econazole nitrate Gramicidin; Halofantrine, halofantrine; Vitamin D2, ergocalciferol hydrochloride; Ergosterol, Haloperidol decanoate; Estradiol benzoate Hexachlorophene; Estradiol cypionate Hexestrol; Estradioldipropionate, estradiol; dipropionate Hexetidine; Estradiol valerate Humulus; Estramustine Hydroxyprogesterone caproate; Ethanolamine oleate Hypericin; Ethopropazine, ethopropazine; hydrochloride Implitapide; Ethyl icosapentate, eicosapentaenoic; acid ethyl ester, ethyl Indigosol Indocyanine green Mitotane; Iocarmate meglumine Mometasone furoate; Iodipamide Monoxychlorosene; Iodoalphionic acid Montelukast, montelukast sodium; Iodoxamate meglumine Motexafin gadolinium; Iophendylate Myristyl alcohol; Isobutylsalicyl cinnamate Nabilone Itraconazole Naftifine, naftifine hydrochloride; Levomethadone Nandrolone decanoate; Linoleic acid, Nandrolone phenpropionate; N-myristyl-3-hydroxybutylamine; Lucanthone, lucanthone hydrochloride hydrochloride 1 mg, n myristyl 3; Nonoxynol 9, nonoxynol, nonoxynol; Meclizine, meclizine hydrochloride 10, nonoxynol 15, nonoxynol 30, Meclofenamic acid, meclofenamate, meclofenamate sodium Octicizer; Mefenamic acid Octyl methoxycinnamate; Menthyl salicylate Oleic acid Mercuriclinoleate Omega 3 acid ethyl esters; Mercury oleate Orlistat; Mestilbol 5 mg, mestilbol Oxiconazole, oxiconazole nitrate; Methixene, methixene hydrochloride Oxychlorosene; Mibefradil, mibefradil dihydrochloride Pararosaniline pamoate; Miconazole Penicillin v hydrabamine; Mifepristone Perflubron Perhexiline, perhexiline maleate Rose bengal, rose bengal sodium Permethrin Sertaconazole; Vitamin K, phytonadione Sertraline, sertraline hydrochloride Pimecrolimus Sibutramine, sibutramine hydrochloride; Pimozide Rapamycin, sirolimus, rapamune; Polyethylene, Sitosterol, sitosterols; Sodium beta-(3,5-diiodo-4-; Polyvinyl n-octadecyl carbamate hydroxyphenyl)atropate, Sodium dodecylbenzenesulfonate ng, Porfimer, porfimer sodium dodecylbenzenesulfonic acid; Posaconazole Sodium oleate; Tetradecylsulfate, sodium tetradecyl; Potassium oleate sulfate; Potassium ricinoleate Sorbitan-sesquioleate; Potassium stearate Stearic acid; Prednimustine Sulconazole, sulconazole nitrate; Probucol Suramin, suramin hexasodium; Progesterone caproate Tacrolimus; Promethestrol dipropionate Tamoxifen, tamoxifen citrate; Pyrrobutamine phosphate Tannic acid; Quazepam Tazarotene; Quinacrine, quinacrine hydrochloride Telithromycin Quinestrol Telmisartan; Raloxifene, raloxifene hydrochloride Temoporfin; Ritonavir Temsirolimus, tezacitabine Terbinafine Tyropanoate, tyropanoate sodium; Terconazole Ubidecarenone, coenzyme Q1Q; Terfenadine Verapamil, dexyerapamil; Testosterone cypionate Verteporfin Testosterone enanthate Vitamin A acetate; Vitamin A palmitate; Testosterone phenylacetate; Tetradecylamine lauryl sarcosinate Zafirlukast Thioridazine Cetyl myristate; Thymol iodide Cetyl myristoleate Tioconazole Docosahexanoic acid, doconexent; Tipranavir Hemin Tiratricol Lutein; Tocopherols excipient Chlorophyll b from spinach Tolnaftate Gossypol; Tolterodine Imipramine pamoate; Toremifene, toremifene citrate Iodipamide meglumine; Alitretinoin, isotretinoin, neovitamin A; retinoic acid, tretinoin, 9-cis-retinoic Ondascora; Tribromsalan Zinc stearate; Phenylbutazone, phenylbutazone; Triolein I 125 isomer; Triparanol Bryo statin-1; Troglitazone Dexanabinol; Tyloxapol Dha-paclitaxel Disaccharide tripeptide glycerol; dipalmitoyl Tetraiodothyroacetic acid; and (NZ)-N-[10,13-dimethyl-17-(6-Oxiconazole nitrate methylheptan-2-yl)-Sarsasapogenin.

In a preferred aspect, the hydrophobic drug is Camptothecin or a Camphtothecin analog, 5 Fluorouracil, Taxol, or vinblastin.

Amino Acid or Peptide (AA)

In the disclosed conjugate, the hydrophobic drug is linked to a single amino acid residue or an amino acid residue of a peptide. This component is shown as AA in Formula I. The particular amino acid or peptide should be hydrophilic so that the conjugate will self assemble in aqueous environments into the nanotube wall. When using a peptide, one or more amino acid residues in the peptide can be hydrophobic or neutral, as long as the overall peptide component is hydrophilic.

The amino acids in Table 1 can be present as residues in the peptide component of the disclosed conjugates.

TABLE 1

Amino Acid Abbreviations

| Amino Acid | Abbreviations |
| --- | --- |
| alanine | Ala (A) |
| allosoleucine | AIle |
| arginine | Arg (R) |
| asparagine | Asn (N) |
| aspartic acid | Asp (D) |
| cysteine | Cys (C) |
| glutamic acid | Glu (E) |
| glutamine | Gln (K) |
| glycine | Gly (G) |
| histidine | His (H) |
| isolelucine | Ile (I) |
| leucine | Leu (L) |
| lysine | Lys (K) |
| phenylalanine | Phe (F) |
| methionine | Met (M) |
| proline | Pro (P) |
| pyroglutamic acid | PGlu |
| serine | Ser (S} |
| threonine | Thr (T) |
| tyrosine | Tyr (Y) |
| tryptophan | Trp (W) |
| valine | Val (V) |

When a single amino acid residue is present in the conjugate, the preferred residues are arginyl, histidyl, lysyl, aspartyl, glutamyl, seryl, threonyl, cystyl, asparagyl, glutaminyl, prolyl, tyrosyl, methionyl, and tryptophanyl. These moieties can be attached to the hydrophobic by a linker at the amino group, the carboxylate group, or the side chain. In certain, examples, the amino acid residue is a lysyl.

When two amino acid residues are present in the conjugate and they are coupled by a peptide bond, the resulting dipeptide can contain any of the residues in Table 1 as long as the overall dipeptide is hydrophilic. For example, the dipeptide can comprise two arginyls, histidyls, lysyls, aspartyls, glutamyls, seryls, threonyls, cystyls, asparagyls, glutaminyls, prolyls, tyrosyls, methionyls, or tryptophanyls. In other examples the dipeptide comprises at least one of arginyl, histidyl, lysyl, aspartyl, glutamyl, seryl, threonyl, cystyl, asparagyl, glutaminyl, prolyl, tyrosyl, methionyl, or tryptophanyl.

In other examples, the didpetide can comprise arginyl with alanyl, allosoleucyl, asparagyl, aspartyl, cystyl, glutamyl, glutaminyl, glycyl, histidyl, isolelucyl, leucyl, lysyl, methionyl, phenylalanyl, prolyl, pyroglutamyl, seryl, threonyl, tyrosyl, tryptophanyl, or valyl.

In other examples, the didpetide can comprise histidyl with alanyl, allosoleucyl, arginyl, asparagyl, aspartyl, cystyl, glutamyl, glutaminyl, glycyl, isolelucyl, leucyl, lysyl, methionyl, phenylalanyl, prolyl, pyroglutamyl, seryl, threonyl, tyrosyl, tryptophanyl, or valyl.

In other examples, the didpetide can comprise lysyl with alanyl, allosoleucyl, arginyl, asparagyl, aspartyl, cystyl, glutamyl, glutaminyl, glycyl, histidyl, isolelucyl, leucyl, methionyl, phenylalanyl, prolyl, pyroglutamyl, seryl, threonyl, tyrosyl, tryptophanyl, or valyl.

In other examples, the didpetide can comprise aspartyl with alanyl, allosoleucyl, arginyl, asparagyl, cystyl, glutamyl, glutaminyl, glycyl, histidyl, isolelucyl, leucyl, lysyl, methionyl, phenylalanyl, prolyl, pyroglutamyl, seryl, threonyl, tyrosyl, tryptophanyl, or valyl.

In other examples, the didpetide can comprise glutamyl with alanyl, allosoleucyl, arginyl, asparagyl, aspartyl, cystyl, glutaminyl, glycyl, histidyl, isolelucyl, leucyl, lysyl, methionyl, phenylalanyl, prolyl, pyroglutamyl, seryl, threonyl, tyrosyl, tryptophanyl, or valyl.

In other examples, the didpetide can comprise seryl with alanyl, allosoleucyl, arginyl, asparagyl, aspartyl, cystyl, glutamyl, glutaminyl, glycyl, histidyl, isolelucyl, leucyl, lysyl, methionyl, phenylalanyl, prolyl, pyroglutamyl, threonyl, tyrosyl, tryptophanyl, or valyl.

In other examples, the didpetide can comprise threonyl with alanyl, allosoleucyl, arginyl, asparagyl, aspartyl, cystyl, glutamyl, glutaminyl, glycyl, histidyl, isolelucyl, leucyl, lysyl, methionyl, phenylalanyl, prolyl, pyroglutamyl, seryl, tyrosyl, tryptophanyl, or valyl.

In other examples, the didpetide can comprise cystyl with alanyl, allosoleucyl, arginyl, asparagyl, aspartyl, glutamyl, glutaminyl, glycyl, histidyl, isolelucyl, leucyl, lysyl, methionyl, phenylalanyl, prolyl, pyroglutamyl, seryl, threonyl, tyrosyl, tryptophanyl, or valyl.

In other examples, the didpetide can comprise asparagyl with alanyl, allosoleucyl, arginyl, aspartyl, glutamyl, glutaminyl, glycyl, histidyl, isolelucyl, leucyl, lysyl, methionyl, phenylalanyl, prolyl, pyroglutamyl, seryl, cystyl threonyl, tyrosyl, tryptophanyl, or valyl.

In other examples, the didpetide can comprise glutaminyl with alanyl, allosoleucyl, arginyl, asparagyl, aspartyl, glutamyl, glycyl, histidyl, isolelucyl, leucyl, lysyl, methionyl, phenylalanyl, prolyl, pyroglutamyl, seryl, cystyl threonyl, tyrosyl, tryptophanyl, or valyl.

In other examples, the didpetide can comprise prolyl with alanyl, allosoleucyl, arginyl, asparagyl, aspartyl, glutamyl, glutaminyl, glycyl, histidyl, isolelucyl, leucyl, lysyl, methionyl, phenylalanyl, pyroglutamyl, seryl, cystyl, threonyl, tyrosyl, tryptophanyl, or valyl.

In other examples, the didpetide can comprise tyrosyl with alanyl, allosoleucyl, arginyl, asparagyl, aspartyl, glutamyl, glutaminyl, glycyl, histidyl, isolelucyl, leucyl, lysyl, methionyl, phenylalanyl, prolyl, pyroglutamyl, seryl, cystyl, threonyl, tryptophanyl, or valyl.

In other examples, the didpetide can comprise methionyl with alanyl, allosoleucyl, arginyl, asparagyl, aspartyl, glutamyl, glutaminyl, glycyl, histidyl, isolelucyl, leucyl, lysyl, phenylalanyl, prolyl, pyroglutamyl, seryl, cystyl threonyl, tyrosyl, tryptophanyl, or valyl.

In other examples, the didpetide can comprise tryptophanyl with alanyl, allosoleucyl, arginyl, asparagyl, aspartyl, glutamyl, glutaminyl, glycyl, histidyl, isolelucyl, leucyl, lysyl, phenylalanyl, prolyl, pyroglutamyl, seryl, cystyl threonyl, tyrosyl, or valyl.

A preferred dipeptide is lysyl-lysyl (KK).

The disclosed conjugate can also comprise three amino acid residues, a tripeptide, linked to the hydrophobic drug. Suitable tripeptides include Xaa-Xbb-Xbb, Xbb-Xaa-Xbb, or Xbb-Xbb-Xaa, where Xaa is arginyl, histidyl, lysyl, aspartyl, glutamyl, seryl, threonyl, cystyl, asparagyl, glutaminyl, prolyl, tyrosyl, methionyl, and tryptophanyl; and wherein each Xbb is independent of the others; alanyl, allosoleucyl, arginyl asparagyl, aspartyl, cystyl, glutamyl, glutaminyl, glycyl, histidyl, isolelucyl, leucyl, lysyl, methionyl, phenylalanyl, prolyl, pyroglutamyl, seryl, threonyl, tyrosyl, tryptophanyl, or valyl.

The disclosed conjugate can also comprise four amino acid residues, a tetrapeptide, linked to the hydrophobic drug. Suitable tetrapeptides include Xaa-Xaa-Xbb-Xbb (SEQ ID NO:2), Xaa-Xbb-Xaa-Xbb (SEQ ID NO:3), Xbb-Xbb-Xaa-Xaa (SEQ ID NO:4), or Xbb-Xaa-Xbb-Xaa (SEQ ID NO:5), where each Xaa is independent of the other, arginyl, histidyl, lysyl, aspartyl, glutamyl, seryl, threonyl, cystyl, asparagyl, glutaminyl, prolyl, tyrosyl, methionyl, and tryptophanyl; and wherein each Xbb is independent of the others, alanyl, allosoleucyl, arginyl asparagyl, aspartyl, cystyl, glutamyl, glutaminyl, glycyl, histidyl, isolelucyl, leucyl, lysyl, methionyl, phenylalanyl, prolyl, pyroglutamyl, seryl, threonyl, tyrosyl, tryptophanyl, or valyl.

In still other examples the conjugate can also comprise five amino acid residues (i.e., a pentapeptide), six amino acid residues (a hexapeptide), seven amino acid residues (a heptapeptide), or eight amino acid residue (an octopeptide). In these examples, the peptide has at least three amino acid residues selected from the group consisting of arginyl, histidyl, lysyl, aspartyl, glutamyl, seryl, threonyl, cystyl, asparagyl, glutaminyl, prolyl, tyrosyl, methionyl, and tryptophanyl.

In many examples herein the conjugate does not contain nine or more amino acid residues.

In each example of the disclosed conjugates, the hydrophobic drug can be linked to the peptide at the side chain of one of the amino acid residues. Further, the peptide component can be functionalized, at one or more side chains or at the C or N terminus. For example, the N terminus of the peptide or amino group on a side chain can be protected with a benzoyloxycarbonyl groups, tert-butoxycarbonyl groups, acetate, trifluoroacetate, 9-fluorenylmethyloxycarbonyl, or 2-bromobenzyloxycarbonyl, or N-hydroxysuccinimide, In further examples, the C terminus or relevant side chain can be protected with a methyl, ethyl, t-butyl, or benzyl ester. In a preferred example, the N terminus of the peptide is protected with a 9-fluorenylmethyloxycarbonyl.

Linker (L)

As noted herein, the disclosed conjugate comprises a hydrophobic drug linked to a single amino acid residue or an amino acid residue of a peptide via a linker moiety. The linker moiety is shown as L in Formula I. The linker moiety of the disclosed conjugates can arise from any compound (linker) that forms a bond with the hydrophobic drug and an amino acid residue, linking them together. Thus, a linker typically contains at least two functional groups, e.g., one functional group that can be used to form a bond with the hydrophobic drug and another functional group that can be used to form a bond with an amino acid residue. Typically, though not necessarily, the functional group on the linker that is used to form a bond with the hydrophobic group is at one end of the linker and the functional group that is used to form a bond with the amino acid is at the other end of the linker.

In some aspects, the linker can comprise electrophilic functional groups that can react with nucleophilic functional groups like hydroxyl, thiol, carboxylate, amino, or amide groups on the hydrophobic drug, forming a bond. Conversely, the linker can comprise nucleophilic functional groups that can react with electrophilic functional groups like carbonyl, halide, or alkoxyl groups on the hydrophobic drug.

The linker can also have one or more electrophilic groups that can react with and thus form a bond to an amino acid residue.

These bonds can be formed by reaction methods known in the art. For example, the hydrophobic drug can be first attached to the linker, followed by attaching the amino acid residue. Alternatively, the linker can be first attached to the amino acid residue and then attached to the hydrophobic drug. Still further, the hydrophobic drug and amino acid residue can both be attached to the linker simultaneously.

The resulting bond between the linker and the hydrophobic drug and amino acid residue should be biodegradable. In this way the drug can be released to the individual and act in its intended way. As such, the bond between the drug and linker, and the bond between the linker and the amino acid residue should be an ester, ether, or amide bond. In many examples herein, the linker moiety does not contain a disulfide bond.

The linker moiety can be of varying lengths, such as from 1 to 20 atoms in length. For example, the linker moiety can be from 1, 2, 3, 4, 5, 6, 7, 8, 9, 10, 11, 12, 13, 14, 15, 16, 17, 18, 19, or 20 atoms in length, where any of the stated values can form an upper and/or lower end point of a range. Further, the linker moiety can be substituted or unsubstituted. When substituted, the linker can contain substituents attached to the backbone of the linker or substituents embedded in the backbone of the linker. For example, an amine substituted linker moiety can contain an amine group attached to the backbone of the linker or a nitrogen in the backbone of the linker.

Suitable linker moieties include, but are not limited to, substituted or unsubstituted, branched or unbranched, alkyl, alkenyl, or alkynyl groups, ethers, esters, polyethers, polyesters, polyalkylenes, polyamines, heteroatom substituted alkyl, alkenyl, or alkynyl groups, cycloalkyl groups, cycloalkenyl groups, heterocycloalkyl groups, heterocycloalkenyl groups, and the like, and derivatives thereof, where the point of attachment to the hydrophobic drug and/or amino acid is an ester, ether, carboxylate, amine, or amide bond.

In one aspect, the linker moiety can comprise a $C_1$-$C_6$ branched or straight-chain alkyl, such as methyl, ethyl, n-propyl, iso-propyl, n-butyl, iso-butyl, sec-butyl, tert-butyl, n-pentyl, iso-pentyl, neopentyl, or hexyl. In a specific example, the linker moiety can comprise $—(CH_2)_m—$, wherein m is from 1 to 10, and where the point of attachment to the hydrophobic drug and/or amino acid is an ester, ether, carboxylate, amine, or amide bond. For example, the linker moiety can be $X^1—(CH_2)_m—X^2$, wherein m is from 1 to 10, and $X^1$ and $X^2$ are, independent of the other, C(O), C(O)O, C(O)N, NH, or O.

In still another aspect, the linker moiety can comprise a $C_2$-$C_6$ branched or straight-chain alkyl, wherein one or more of the carbon atoms is substituted with oxygen (e.g., an ether) or an amino group. For example, suitable linkers can include, but are not limited to, a methoxymethyl, methoxyethyl, methoxypropyl, methoxybutyl, ethoxymethyl, ethoxyethyl, ethoxypropyl, propoxymethyl, propoxyethyl, methylaminomethyl, methylaminoethyl, methylaminopropyl, methylaminobutyl, ethylaminomethyl, ethylaminoethyl, ethylaminopropyl, propylaminomethyl, propylaminoethyl, methoxymethoxymethyl, ethoxymethoxymethyl, methoxyethoxymethyl, methoxymethoxyethyl, and the like, and derivatives thereof, where the point of attachment to the hydrophobic drug and/or amino acid is an ester, ether, or amide bond.

In a preferred example, the linker moiety is —C(O)CH$_2$CH$_2$C(O)—, i.e., a succinate ester.

Specific Examples

In specific examples of the disclosed conjugates, and thus nanotubes comprising them, is a conjugate of Formula I wherein L is a C$_1$-C$_6$ alkyldiester, and AA is KK or KFKK (SEQ ID NO:6), protected or unprotected with one or more acetate or 9-fluorenylmethyloxycarbonyl groups.

In other specific examples, the hydrophobic drug is Camptothecin (CPT) or a CPT analog. CPT can be linked to the ε-amino group of lysine via a linker such as a succinate ester. It is demonstrated herein that CPT- or CPT analog-peptide conjugates self assemble into well-defined nanotubes. The mass of these nanotubes is primarily comprised of the CPT or CPT analog, and hydrolytic degradation of the peptide portion produces only the CPT/CPT analog and biocompatible amino acid components. These conjugates are shown herein to be effective in killing human colorectal cancer cells in vitro, and all assemblies exhibited greater potency than the clinically used Irinotecan. The conjugates induced cell death for human colorectal cells at concentrations much lower than required for clinically used Irinotecan.

With CPT or CPT analogs, the amino acid residue can be linked to the CPT or CPT analog via a linker at the 20-position. Esterification of the 20-position hydroxyl group is often used to conjugate CPT to other molecule because this linkage is cleaved under physiological conditions. It has been reported that the free 20-hydroxyl group may facilitate the opening reaction of the E-ring lactone through intramolecular hydrogen bonding with the carbonyl moiety (Fassberg et al., id; Henne et al., Synthesis and activity of a folate peptide camptothecin prodrug. *Bioorg Med Chem Lett* 2006, 16, 5350). Thus, CPT prodrugs esterified at the 20-hydroxyl position generally exhibit greater lactone stability and decreased cytotoxicity compared with unmodified CPT (Cao et al., Alkyl esters of Camptothecin and 9-nitrocamptothecin: Synthesis, in vitro pharmacokinetics, toxicity, and antitumor activity. *J Med Chem* 1998, 41, 31; Vishnuvajjala et al., Tricyclo[4.2.2.02,5]Dec-9-Ene-3,4,7,8-Tetracarboxylic Acid Diimide—Formulation and Stability Studies. *J Pharm Sci* 1986, 75, 301; Conover et al., Camptothecin delivery systems: enhanced efficacy and tumor accumulation of Camptothecin following its conjugation to polyethylene glycol via a glycine linker. *Cancer Chemoth Pharm* 1998, 42, 407; Scheeren et al., Novel 20-carbonate linked prodrugs of camptothecin and 9-aminocamptothecin designed for activation by tumour-associated plasmin. *Bioorg Med Chem Lett* 2002, 12, 2371; Yang et al., Novel camptothecin derivatives. Part 1: Oxyalkanoic acid esters of Camptothecin and their in vitro and in vivo antitumor activity. *Bioorg Med Chem Lett* 2002, 12, 1241; Sinka et al., id). It has also been shown that a succinate linkage at the 20-position system of CPT offers relatively high hydrolytic stability (Dosio et al., Preparation, characterization and properties in vitro and in vivo of a paclitaxel-albumin conjugate. *J Control Release* 1997, 47, 293; Cattel et al., Preparation, characterization and properties of sterically stabilized paclitaxel-containing liposomes. *J Control Release* 2000, 63, 19; Safavy et al., Site-specifically traced drug release and biodistribution of a paclitaxel-antibody conjugate toward improvement of the linker structure. *Bioconjugate Chem* 2004, 15, 1264; Audus et al., Chemical modification of paclitaxel (Taxol) reduces P-glycoprotein interactions and increases permeation across the blood-brain barrier in vitro and in situ. *J Med Chem* 2005, 48, 832).

In certain examples, disclosed herein are conjugates having Formula II:

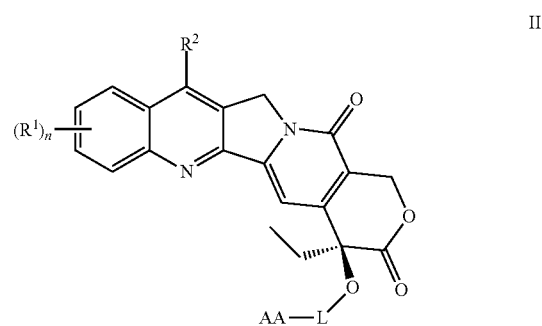

where n is from 1 to 4, each R$^1$ and R$^2$ are, independent of one another, H, OH, lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen or deuterium, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, N$_3$, SH, SCH$_3$, C(O)CH$_3$, CO$_2$CH$_3$, or CO$_2$H, or together two R$^1$ or one R$^1$ and R$^2$ can form a fused cycloalkyl or cycloheteroalkyl;

L is a linker moiety as described herein; and

AA is a single amino acid or a peptide as described herein.

In some examples the CPT analog is Topotecan, Ionotecan, Exatecan, Lurtotecan, DB 67, DNP 1350, ST 1481, or CKD 602.

In specific examples, the conjugate can have Formula II-A through II-E

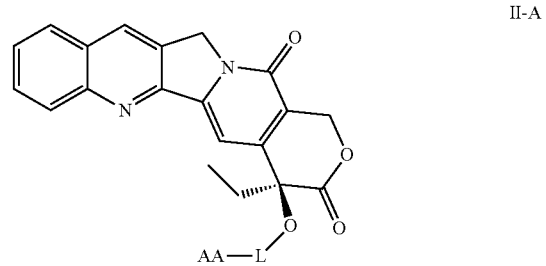

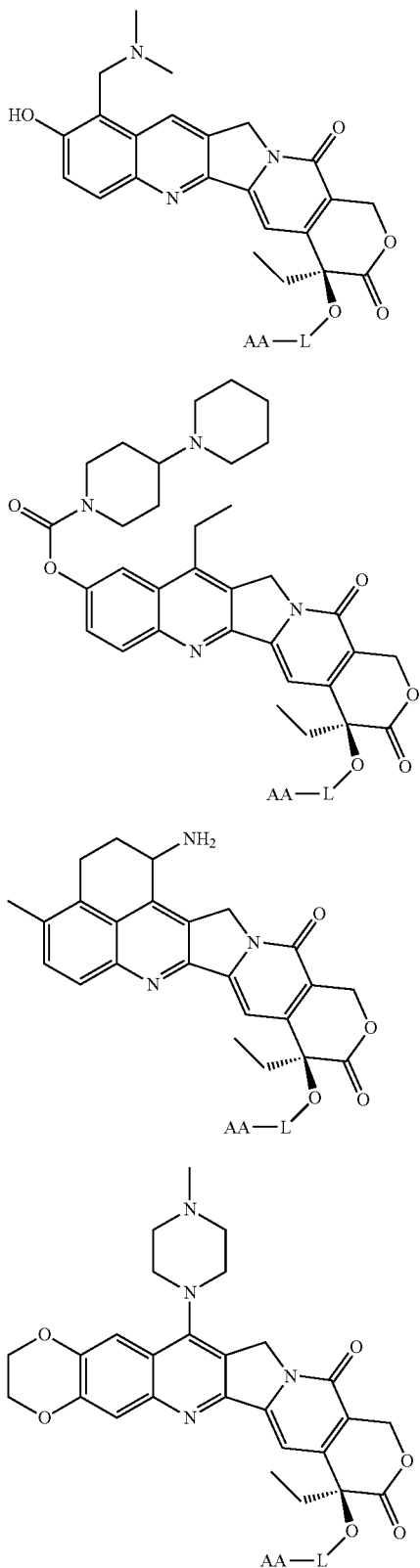

independent of the other, C(O), C(O)O, or C(O)N. In other examples, L can be C(O)—(CH$_2$)$_m$—C(O), where m is from 1 to 6.

In the conjugates of Formula II, AA can be any of the amino acids or peptides disclosed herein. For example, AA can be protected or unprotected lysyl, lysyl-lysyl, lysyl-phenylalanyl-lysyl-lysyl (SEQ ID NO:6).

Also contemplated are nanotubes comprises conjugates of Formula II as herein disclosed.

Other conjugates disclosed herein include taxol or vinblastine or 5-fluorouracil as the hydrophobic drug component, which is linked to AA as described herein.

Methods of Use

The disclosed conjugates and nanotubes made from them can be administered and used in a manner consistent with that of the original hydrophobic drug. For example, disclosed herein are methods of treating or preventing cancer in a subject, comprising administering to the subject a therapeutically effective amount of a conjugate or nanotube as disclosed herein. Additionally, the method can further comprise administering a therapeutically effective amount of ionizing radiation to the subject. The disclosed conjugate or nanotube are suitable for cancers, such as, but not limited to, pancreatic cancer, breast cancer, lung cancer, prostrate cancer, ovarian cancer, colon cancer, gastric cancer, head and neck cancer, melanoma, leukemia, multiple myeloma or lypmpoma.

Methods of killing a tumor cell are also provided herein. The methods comprise contacting a tumor cell with an effective amount of a conjugate or nanotube as disclosed herein. The methods can further include administering a second compound or composition (e.g., an anticancer agent) or administering an effective amount of ionizing radiation to the subject.

Also provided herein are methods of radiotherapy of tumors, comprising contacting the tumor with an effective amount of a conjugate or nanotube as disclosed herein and irradiating the tumor with an effective amount of ionizing radiation. Methods of treating inflammation in a subject are further provided herein, the methods comprising administering to the subject an effective amount of a conjugate or nanotube as described herein. Optionally, the methods can further include administering a second compound or composition (e.g., an anti-inflammatory agent).

The disclosed subject matter also concerns methods for treating a subject having an oncological disorder or condition. In one embodiment, an effective amount of one or more conjugate or nanotube disclosed herein is administered to a subject having an oncological disorder and who is in need of treatment thereof. The disclosed methods can optionally include identifying a subject who is or can be in need of treatment of an oncological disorder. The subject can be a human or other mammal, such as a primate (monkey, chimpanzee, ape, etc.), dog, cat, cow, pig, or horse, or other animals having an oncological disorder. Means for administering and formulating compounds for administration to a subject are known in the art, examples of which are described herein. Oncological disorders include, but are not limited to, cancer and/or tumors of the anus, bile duct, bladder, bone, bone marrow, bowel (including colon and rectum), breast, eye, gall bladder, kidney, mouth, larynx, esophagus, stomach, testis, cervix, head, neck, ovary, lung, mesothelioma, neuroendocrine, penis, skin, spinal cord, thyroid, vagina, vulva, uterus, liver, muscle, pancreas, prostate, blood cells (including lymphocytes and other immune system cells), and brain. Specific cancers contemplated for treatment include carcinomas, Karposi's sarcoma, mela- In the conjugates of Formula II, L can be any of the linker moieties described herein. For example, L can be X$^1$—(CH$_2$)$_m$—X$^2$, wherein m is from 1 to 10 and X$^1$ and X$^2$ are, noma, mesothelioma, soft tissue sarcoma, pancreatic cancer, lung cancer, leukemia (acute lymphoblastic, acute myeloid, chronic lymphocytic, chronic myeloid, and other), and lymphoma (Hodgkin's and non-Hodgkin's), and multiple myeloma.

Other examples of cancers that can be treated according to the methods disclosed herein are adrenocortical carcinoma, adrenocortical carcinoma, cerebellar astrocytoma, basal cell carcinoma, bile duct cancer, bladder cancer, bone cancer, brain tumor, breast cancer, Burkitt's lymphoma, carcinoid tumor, central nervous system lymphoma, cervical cancer, chronic myeloproliferative disorders, colon cancer, cutaneous T-cell lymphoma, endometrial cancer, ependymoma, esophageal cancer, gallbladder cancer, gastric (stomach) cancer, gastrointestinal carcinoid tumor, germ cell tumor, glioma, hairy cell leukemia, head and neck cancer, hepatocellular (liver) cancer, hypopharyngeal cancer, hypothalamic and visual pathway glioma, intraocular melanoma, retinoblastoma, islet cell carcinoma (endocrine pancreas), laryngeal cancer, lip and oral cavity cancer, liver cancer, medulloblastoma, Merkel cell carcinoma, squamous neck cancer with occult mycosis fungoides, myelodysplastic syndromes, myelogenous leukemia, nasal cavity and paranasal sinus cancer, nasopharyngeal cancer, neuroblastoma, non-small cell lungcancer, oral cancer, oropharyngeal cancer, osteosarcoma, ovarian cancer, pancreatic cancer, paranasal sinus and nasal cavity cancer, parathyroid cancer, penile cancer, pheochromocytoma, pineoblastoma and supratentorial primitive neuroectodermal tumor, pituitary tumor, plasma cell neoplasm/multiple myeloma, pleuropulmonary blastoma, prostate cancer, rectal cancer, renal cell (kidney) cancer, retinoblastoma, rhabdomyosarcoma, salivary gland cancer, Ewing's sarcoma, soft tissue sarcoma, Sezary syndrome, skin cancer, small cell lung cancer, small intestine cancer, supratentorial primitive neuroectodermal tumors, testicular cancer, thymic carcinoma, thymoma, thyroid cancer, transitional cell cancer of the renal pelvis and ureter, trophoblastic tumor, urethral cancer, uterine cancer, vaginal cancer, vulvar cancer, Waldenstrom's macroglobulinemia, and Wilms' tumor.

Compositions, Formulations and Methods of Administration

In vivo application of the disclosed compounds, and compositions containing them, can be accomplished by any suitable method and technique presently or prospectively known to those skilled in the art. For example, the disclosed conjugate or nanotube can be formulated in a physiologically- or pharmaceutically-acceptable form and administered by any suitable route known in the art including, for example, oral, nasal, rectal, topical, and parenteral routes of administration. As used herein, the term parenteral includes subcutaneous, intradermal, intravenous, intramuscular, intraperitoneal, and intrasternal administration, such as by injection. Administration of the disclosed conjugate or nanotube can be a single administration, or at continuous or distinct intervals as can be readily determined by a person skilled in the art.

The conjugate or nanotube disclosed herein, and compositions comprising them, can also be administered utilizing liposome technology, slow release capsules, implantable pumps, and biodegradable containers. These delivery methods can, advantageously, provide a uniform dosage over an extended period of time. The compounds can also be administered in their salt derivative forms or crystalline forms.

The conjugate or nanotube disclosed herein can be formulated according to known methods for preparing pharmaceutically acceptable compositions. Formulations are described in detail in a number of sources which are well known and readily available to those skilled in the art. For example, *Remington's Pharmaceutical Science* by E. W. Martin (1995) describes formulations that can be used in connection with the disclosed methods. In general, the conjugate or nanotube disclosed herein can be formulated such that an effective amount of the hydrophobic drug is combined with a suitable carrier in order to facilitate effective administration of the drug. The resulting compositions can be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically-acceptable carriers and diluents which are known to those skilled in the art. Examples of carriers or diluents for use with the compounds include ethanol, dimethyl sulfoxide, glycerol, alumina, starch, saline, and equivalent carriers and diluents. To provide for the administration of such dosages for the desired therapeutic treatment, compositions disclosed herein can advantageously comprise between about 0.1% and 99%, and especially, 1 and 15% by weight of the total of one or more of the hydrophobic drug based on the weight of the total composition including carrier or diluent. The amount of drug relative to the nanotube will be much higher, e.g., greater than 50 wt. % based on the weight of the nanotube.

Formulations suitable for administration include, for example, aqueous sterile injection solutions, which can contain antioxidants, buffers, bacteriostats, and solutes that render the formulation isotonic with the blood of the intended recipient; and aqueous and nonaqueous sterile suspensions, which can include suspending agents and thickening agents. The formulations can be presented in unit-dose or multi-dose containers, for example sealed ampoules and vials, and can be stored in a freeze dried (lyophilized) condition requiring only the condition of the sterile liquid carrier, for example, water for injections, prior to use. Extemporaneous injection solutions and suspensions can be prepared from sterile powder, granules, tablets, etc. It should be understood that in addition to the ingredients particularly mentioned above, the compositions disclosed herein can include other agents conventional in the art having regard to the type of formulation in question.

Conjugates or nanotubes disclosed herein, and compositions comprising them, can be delivered to a cell either through direct contact with the cell or via a carrier means. Carrier means for delivering compounds and compositions to cells are known in the art and include, for example, encapsulating the composition in a liposome moiety. Another means for delivery of compounds and compositions disclosed herein to a cell comprises attaching the compounds to a protein or nucleic acid that is targeted for delivery to the target cell. U.S. Pat. No. 6,960,648 and U.S. Application Publication Nos. 20030032594 and 20020120100 disclose amino acid sequences that can be coupled to another composition and that allows the composition to be translocated across biological membranes. U.S. Application Publication No. 20020035243 also describes compositions for transporting biological moieties across cell membranes for intracellular delivery. The conjugate or nanotube can also be incorporated into polymers, examples of which include poly (D-L lactide-co-glycolide) polymer for intracranial tumors; poly[bis(p-carboxyphenoxy) propane: sebacic acid] in a 20:80 molar ratio (as used in GLIADEL); chondroitin; chitin; and chitosan.

For the treatment of oncological disorders, the conjugate or nanotube disclosed herein can be administered to a patient in need of treatment in combination with other antitumor or anticancer substances and/or with radiation and/or photodynamic therapy and/or with surgical treatment to remove a tumor. These other substances or treatments can be given at the same as or at different times from the compounds disclosed herein. For example, the conjugate or nanotube disclosed herein can be used in combination with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively, or an immunotherapeutic such as ipilimumab and bortezomib.

In certain examples, the conjugate or nanotube disclosed herein can be locally administered at one or more anatomical sites, such as sites of unwanted cell growth (such as a tumor site or benign skin growth, e.g., injected or topically applied to the tumor or skin growth), optionally in combination with a pharmaceutically acceptable carrier such as an inert diluent. Conjugate or nanotube disclosed herein can be systemically administered, such as intravenously or orally, optionally in combination with a pharmaceutically acceptable carrier such as an inert diluent, or an assimilable edible carrier for oral delivery. They can be enclosed in hard or soft shell gelatin capsules, can be compressed into tablets, or can be incorporated directly with the food of the patient's diet. For oral therapeutic administration, the active conjugate or nanotube can be combined with one or more excipients and used in the form of ingestible tablets, buccal tablets, troches, capsules, elixirs, suspensions, syrups, wafers, aerosol sprays, and the like.

The tablets, troches, pills, capsules, and the like can also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring can be added. When the unit dosage form is a capsule, it can contain, in addition to materials of the above type, a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac, or sugar and the like. A syrup or elixir can contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound can be incorporated into sustained-release preparations and devices.

Conjugates or nanotubes disclosed herein, including pharmaceutically acceptable salts, or hydrates thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form should be sterile, fluid and stable under the conditions of manufacture and storage. he liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a conjugate or nanotube disclosed herein in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, a conjugate or nanotube disclosed herein can be applied in as a liquid or solid. However, it will generally be desirable to administer them topically to the skin as compositions, in combination with a dermatologically acceptable carrier, which can be a solid or a liquid. Compositions disclosed herein can be applied topically to a subject's skin to reduce the size (and can include complete removal) of malignant or benign growths, or to treat an infection site. Conjugate or nanotubes disclosed herein can be applied directly to the growth or infection site. Preferably, the conjugate or nanotube is applied to the growth or infection site in a formulation such as an ointment, cream, lotion, solution, tincture, or the like.

Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the conjugates, nanotubes, and pharmaceutical compositions disclosed herein can be determined by comparing their in vitro activity, and in vivo activity in animal models. Methods for the extrapolation of effective dosages in mice, and other animals, to humans are known to the art.

Also disclosed are pharmaceutical compositions that comprise a compound disclosed herein in combination with a pharmaceutically acceptable carrier. Pharmaceutical compositions adapted for oral, topical or parenteral administration, comprising an amount of a compound constitute a preferred aspect. The dose administered to a patient, particularly a human, should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

Kits

The disclosed subject matter also concerns a packaged dosage formulation comprising in one or more containers at least one conjugate or nanotube disclosed herein. A packaged dosage formulation can optionally comprise in one or more containers a pharmaceutically acceptable carrier or diluent. A packaged dosage formulation can also optionally comprise, in addition to a conjugate or nanotube disclosed herein, other therapeutics.

Depending upon the disorder or disease condition to be treated, a suitable dose(s) can be that amount that will reduce proliferation or growth of the target cell(s). In the context of cancer, a suitable dose(s) is that which will result in a concentration of the active agent in cancer tissue, such as a malignant tumor, which is known to achieve the desired response. The preferred dosage is the amount which results in maximum inhibition of cancer cell growth, without unmanageable side effects. Administration of a compound and/or agent can be continuous or at distinct intervals, as can be determined by a person of ordinary skill in the art.

To provide for the administration of such dosages for the desired therapeutic treatment, in some embodiments, pharmaceutical compositions disclosed herein can comprise between about 0.1% and 45%, and especially, 1 and 15%, by weight of the total of one or more of the compounds based on the weight of the total composition including carrier or diluents. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

Also disclosed are kits that comprise a conjugate or nanotube disclosed herein in one or more containers. The disclosed kits can optionally include pharmaceutically acceptable carriers and/or diluents. In one embodiment, a kit includes one or more other components, adjuncts, or adjuvants as described herein. In another embodiment, a kit includes one or more anti-cancer agents, such as those agents described herein. In one embodiment, a kit includes instructions or packaging materials that describe how to administer a compound or composition of the kit. Containers of the kit can be of any suitable material, e.g., glass, plastic, metal, etc., and of any suitable size, shape, or configuration. In one embodiment, a compound and/or agent disclosed herein is provided in the kit as a solid, such as a tablet, pill, or powder form. In another embodiment, a conjugate or nanotube disclosed herein is provided in the kit as a liquid or solution. In one embodiment, the kit comprises an ampoule or syringe containing a compound and/or agent disclosed herein in liquid or solution form.

EXAMPLES

The following examples are set forth below to illustrate the methods, compositions, and results according to the disclosed subject matter. These examples are not intended to be inclusive of all aspects of the subject matter disclosed herein, but rather to illustrate representative methods, compositions, and results. These examples are not intended to exclude equivalents and variations of the present invention, which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

Example 1: Synthesis—CPT-Peptides

Camptothecin was treated with succinic anhydride in the presence of DBU to form the corresponding succinic monoester to provide a free carboxylic acid for attachment to the lysine side chain via amide bond formation (Scheme 1).

Scheme 1.
Synthesis of camptothecin functionalized with succinates on C-20.

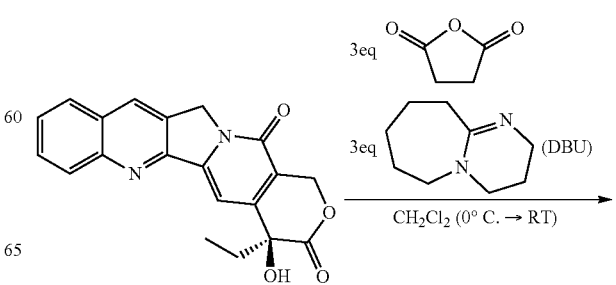

-continued
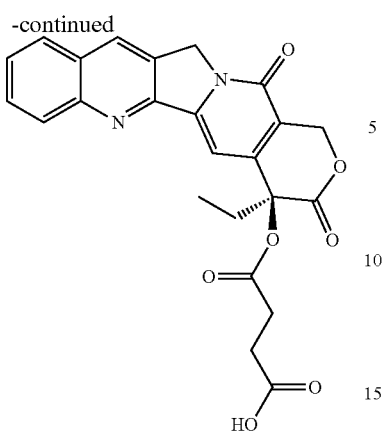
All peptides were manually prepared using Fmoc/t-Bu solid-phase peptide synthesis on Rink amide resin. A series of CPT-peptide conjugates were synthesized via on-resin amidation of the side chain (Scheme 2).

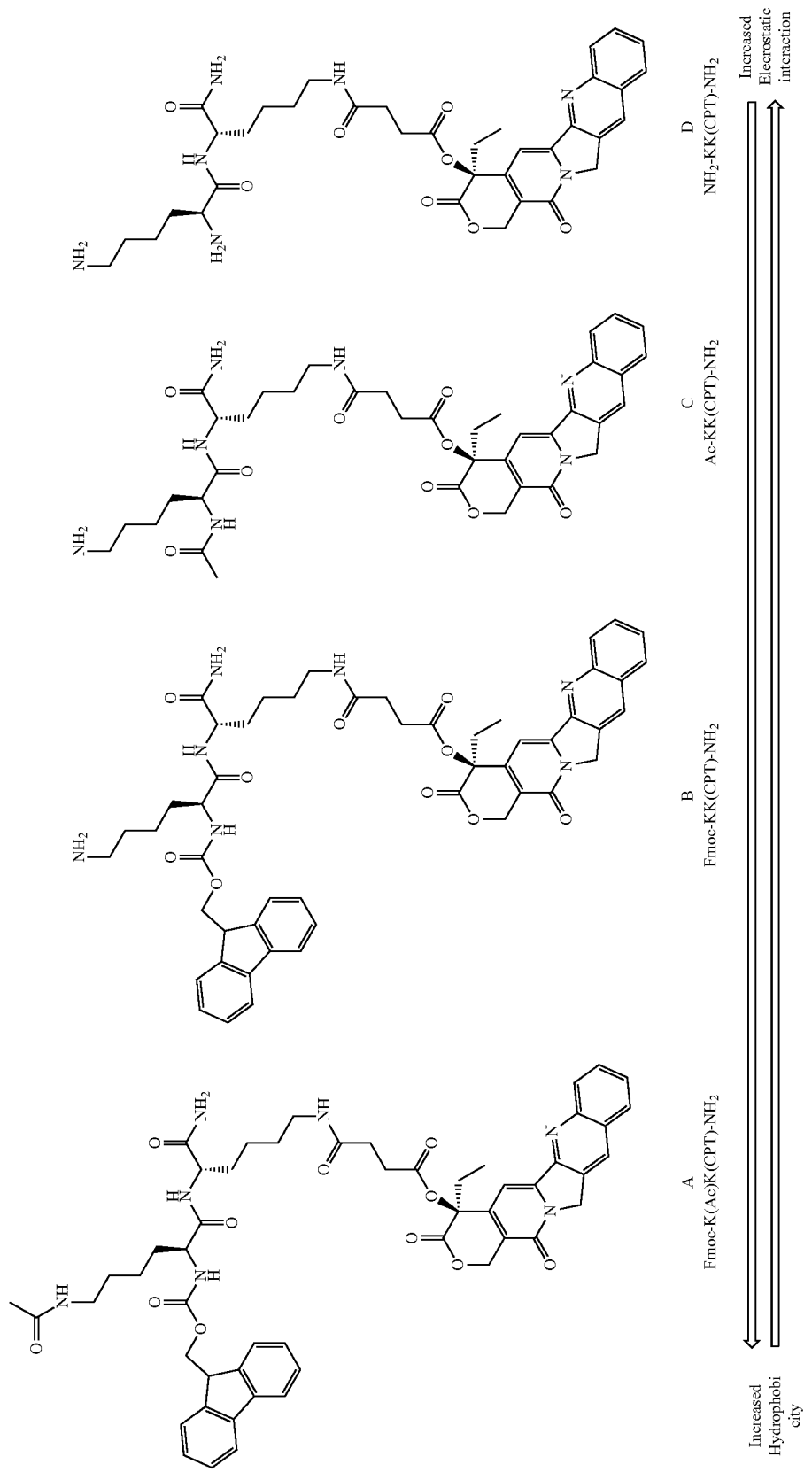
Scheme 2. Chemical structures of Fmoc-K(AcK(CPT)-NH$_2$ (A), Fmoc-KK(CPT)-NH$_2$ (B), Ac-KK(CPT)-NH$_2$ (C), NH$_2$-KK(CPT)-NH$_2$ (D), Fmoc-KFKK(CPT)-NH$_2$ (E), AcKFKK(CPT)-NH$_2$ (F), and NH$_2$-KFKK(CPT)-NH$_2$ (G).

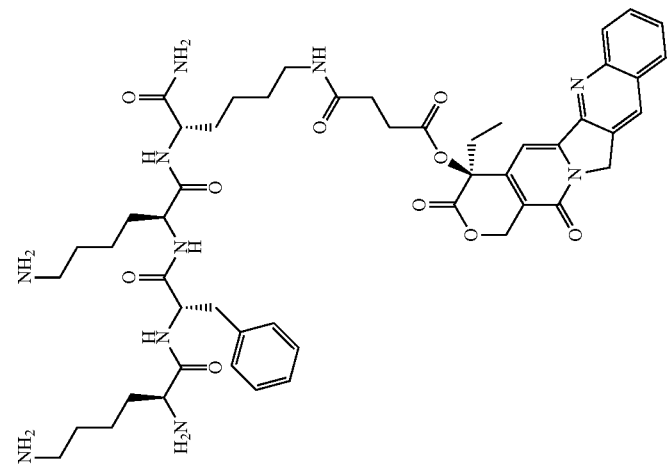
G
NH$_2$-KFKK(CPT)-NH$_2$
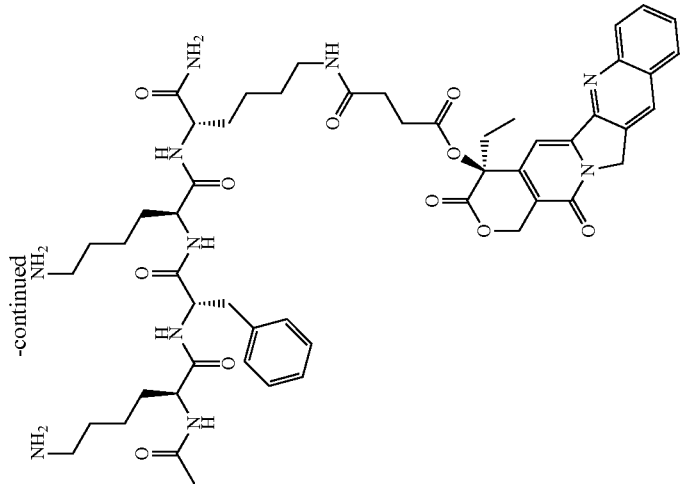
F
Ac-KFKK(CPT)-NH$_2$
CPT-tetrapeptide conjugates
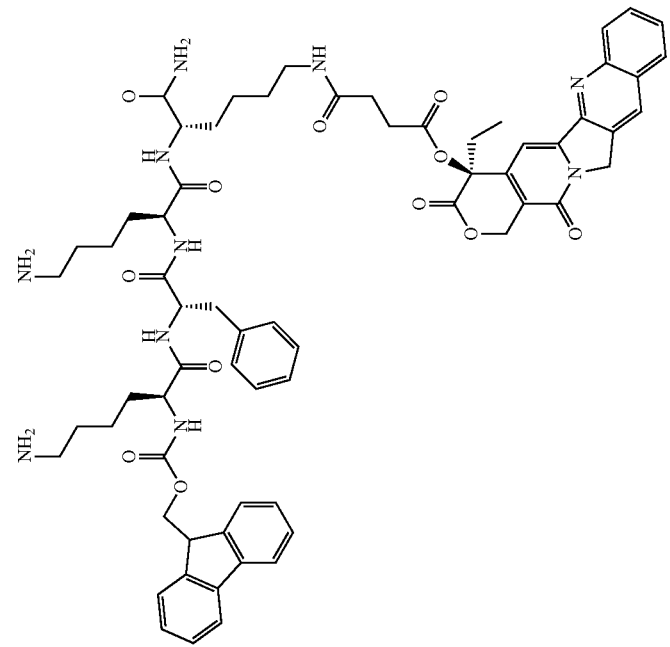
E
Fmoc-KFKK(CPT)-NH$_2$ Scheme 2. Chemical structures of Fmoc-K(Ac)K(CPT)-NH$_2$ (A), Fmoc-KK(CPT)-NH$_2$ (B), Ac-KK(CPT)-NH$_2$ (C), NH$_2$—KK(CPT)-NH$_2$ (D), Fmoc-KFKK(CPT)-NH$_2$ (SEQ ID NO:1) (E), Ac-KFKK(CPT)-NH$_2$ (SEQ ID NO:7) (F), and NH$_2$—KFKK(CPT)-NH$_2$ (SEQ ID NO:8) (G).

Example 2: Self Assembly

Figure 1:
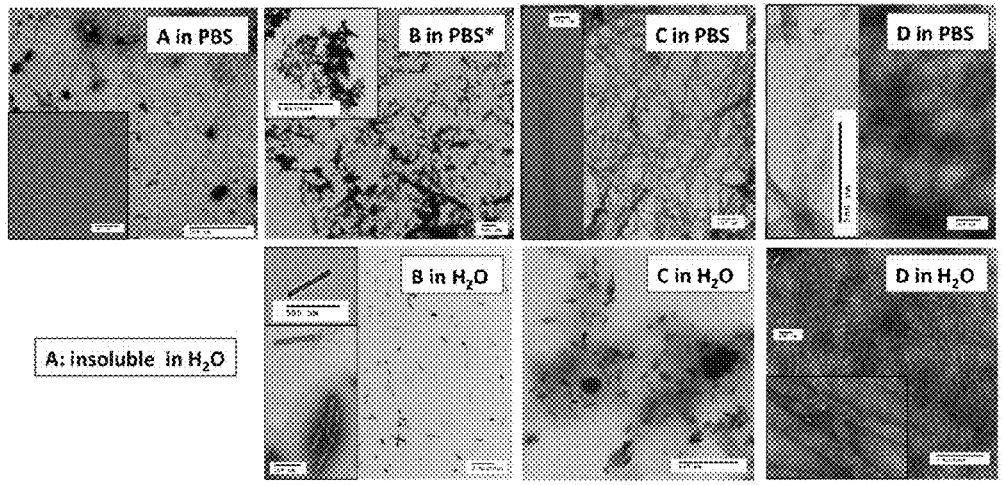
FIG. 1 is a group of TEM images (carbon-coated copper grid, Uranyl acetate as negative stain) of CPT-dipeptides A, B, C, and D in PBS and $H_2O$. The solution was prepared in 10 mM concentration, aged for 3 days, and freshly diluted to 1 mM for the microscopy (Compound B has a poor solubility in PBS). Inset of A in PBS shows zoom-in image of individual nanofibers. Inset of A in both PBS and water displays zoom-in TEM image of nanotubes showing thickness of wall. Inset TEM images of C in PBS and D in both PBS and $H_2O$ shows intermediate structures rolling into nanotubes.
Figure 2:
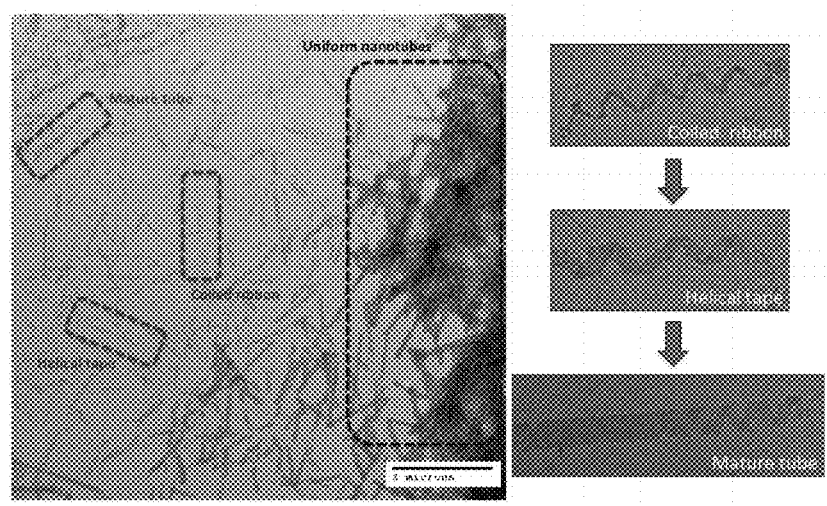
FIG. 2 is a TEM image of C in PBS on the carbon-coated copper grid with a negative stain. The sample was prepared at 10 mM, incubated for 3 days, and freshly diluted to 1 mM. Left: mixture of intermediates such as helical tapes, coiled ribbon, and mature nanotubes. Right: observed TEM images of intermediate structures to support the self-assembly mechanism.
Figure 3:
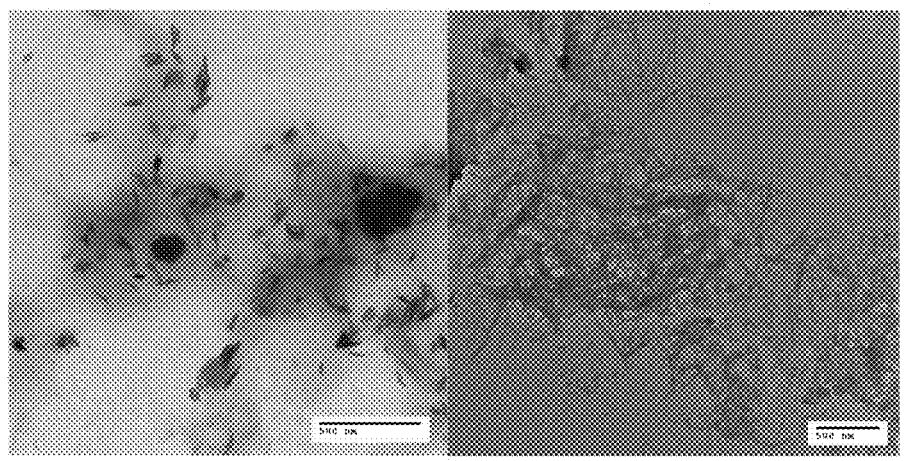
FIG. 3 is a pair of TEM images of CPT-dipeptide C in $H_2O$ (1 mM) solution diluted from 10 mM after (A) 3 days and (B) 2 weeks. Carbon-coated copper grid was used with 2 wt % uranyl acetate as negative stain.

Dipeptide Ac-KK(CPT)-NH$_2$ (C) was constructed and was studied in both H$_2$O and PBS. In PBS, C produced nanotubes with diameters of 80-120 nm (10 mM, FIG. 1) whereas, only non-specific aggregation was observed at 1 mM. However, if 10 mM solutions of C were diluted and imaged at 1 mM in PBS, coiled ribbons and helical tapes could be observed as intermediates leading to the formation of uniform nanotubes (FIG. 2). The similarity of this process to the rolling of bilayer ribbons observed for NDI-lysine amphiphiles in water is noteworthy (Shao et al., Aqueous Self-Assembly of L-Lysine-Based Amphiphiles into 1D n-Type Nanotubes. *Chem-Eur J* 2011, 17, 12882). In pure water, C displayed small portion of short fibers in 3 days that turned into longer fibers after two weeks (FIG. 3), which implies that salts in PBS could accelerate the self-assembly system forming well-organized nano structures.

Figure 4:
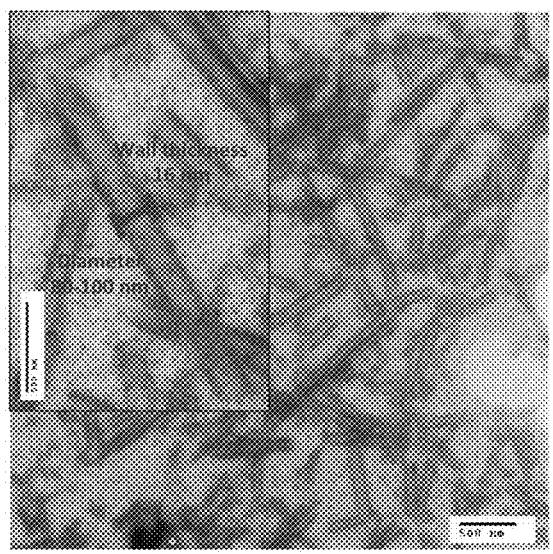
FIG. 4 is a TEM image of compound D in PBS (Carbon-coated copper grid, 2 wt % uranyl acetate as negative stain). The solution was prepared at 10 mM concentration, aged for 3 days, and freshly diluted to 1 mM for the microscopy. Inset: zoom-in image of individual tube showing the thickness of wall and diameter.
Figure 5:
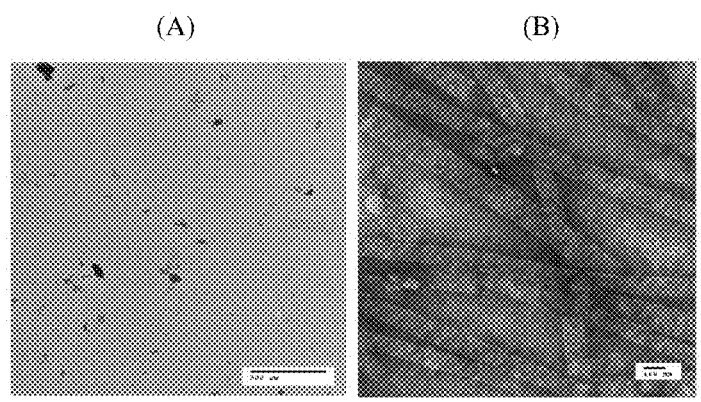
FIG. 5 is a pair of TEM images of CPT-dipeptide D in $H_2O$. Sample solution was prepared with 3 days incubation (A) in 0.25 mM solution and (B) in 10 mM solution. TEM image of (B) was prepared from the diluted solution from 10 mM into 1 mM.

A PBS solution of compound D, NH$_2$—KK(CPT)-NH$_2$, with lower hydrophobicity and increased charge imposed by the additional ammonium group at the N-terminal position of the dipeptide was prepared and incubated for 3 days at 10 mM. As shown in FIG. 1 (D in PBS), the TEM image of D revealed nanotubes with diameters of 80-120 nm and 16 nm wall thicknesses. The presence of helical intermediates suggests an assembly mechanism similar to C (D in PBS, inset). However, no significant assembly was observed from solutions prepared at low concentrations (0.25 mM in PBS). In contrast to dipeptide C, D formed identical nanotubes in both PBS and pure H$_2$O when samples were prepared from 10 mM solutions after 3 days (FIG. 4). However, no assembly was observable in water or PBS at low concentrations (0.25 mM), even after two weeks. TEM images of D in water also revealed helical intermediates (FIG. 5).

Introduction of the Fmoc group promotes the lateral interdigitation of β-sheet structures in dipeptide-NDI conjugates, resulting in the assembly of well-defined nanobelts that formed a self-supporting hydrogel (Shao et al., A pi-conjugated hydrogel based on an Fmoc-dipeptide naphthalene diimide semiconductor. *Chem Commun* 2010, 46, 4285). This design is similar to dipeptide B, (Fmoc-KK(CPT)-NH$_2$), which revealed well-defined nanotubes with diameters of 80-100 nm lengths of about 600 nm, and 16 nm wall thickness of nanotubes in the TEM images of samples prepared in water. However, a mixture of nonspecific aggregation and nanotubes were observed in PBS, likely due to limited solubility of D in PBS. Compared to C and D, assembled structure of B in H$_2$O provided shorter nanotubes but similar wall thicknesses and diameters. It is noteworthy that, similar to the NDI-lysine amphiphiles (Shao et al., 2011, id.), the nanotube assembly of the CPT-peptide conjugates tolerates a wide range of head group structures (-Fmoc, -Acyl, and —NH$_2$).

In order to examine the influence of the charged ammonium side chains, dipeptide A was prepared. TEM imaging revealed fibrillar nanostructures in PBS but no assembly occurred in water, likely due to poor solubility in pure water. The nanofibers obtained from PBS solutions exhibited micrometer long lengths and uniform diameters of 8 nm.

Three CPT-tetrapeptide (KFKK (SEQ ID NO:6)) conjugates were prepared that have alternating hydrophobic and hydrophilic sequence similar to the dipeptide derivatives with one additional lysine bearing a charged free amine. Compound E, F, and G were soluble in both H$_2$O and PBS but as hydrophobicity decreased by changing the N-termini from -Fmoc to —NH$_2$, solubility in both solutions increased. Although tetrapeptide E partially precipitated after one hour in PBS at 10 mM, F and G remained highly soluble in PBS, and all the tetrapeptides were highly soluble in pure water.

Figure 6:
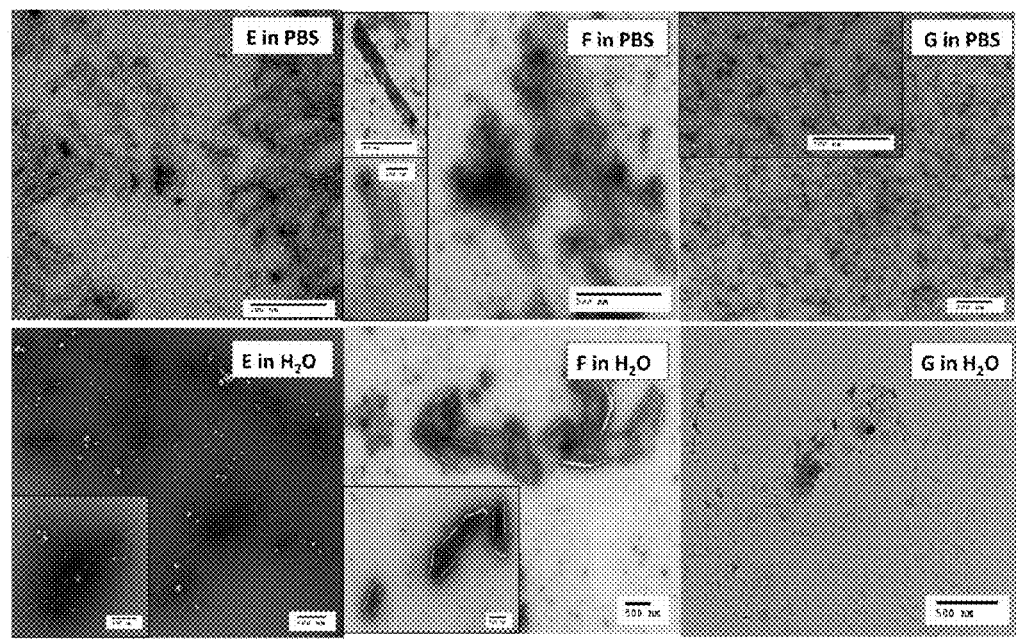
FIG. 6 is a group of TEM images of CPT-tetrapeptides E (Inset of E in $H_2O$: zoom-in image of tubes), F (Inset of F in PBS: zoom-in image of intermediate forming tubes), and G (Inset of G in PBS: zoom-in image of show short and uniform nanofibers) in PBS and $H_2O$. Each solution was prepared at a concentration of 10 mM in either PBS or $H_2O$ with 3 days incubation and then diluted into 1 mM prior to imaging. TEM images were collected on the carbon-coated copper grid with a negative stain.
Figure 7:
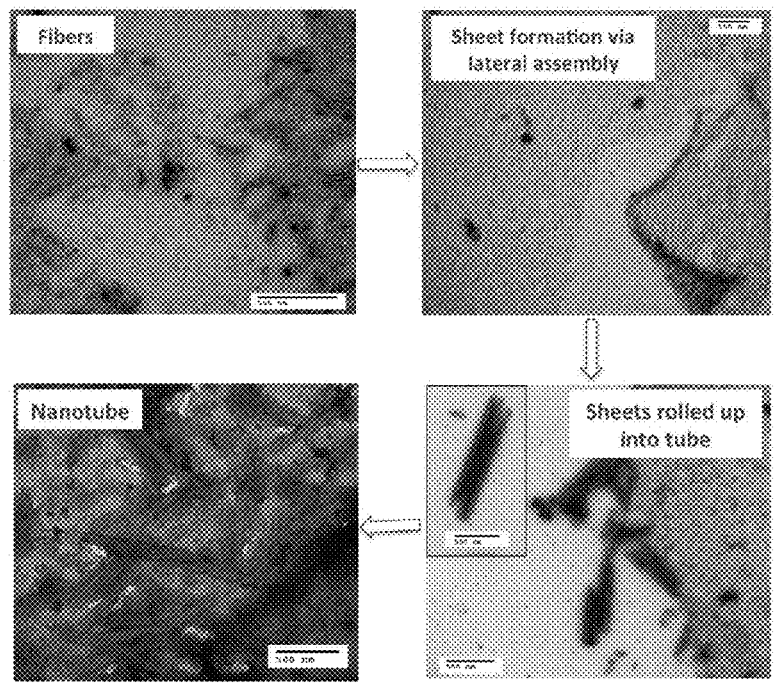
FIG. 7 is a group of TEM images of CPT-tetrapeptides E in PBS by aging and mechanism of self-assembly. Samples were prepared at a concentration of 10 mM in PBS with 3 days incubation and then diluted into 1 mM prior to imaging.

As shown in the FIG. 6, tetrapeptide E formed uniform, micrometer-long nanofibers in PBS with diameters of about 15 nm. It is noteworthy that the assembly of E was very sensitive to concentration and aging time. At low concentrations (0.5 mM in PBS), poorly formed, ragged fibers were observed; at higher concentration (10 mM in PBS), uniform nanofibers formed and persisted after dilution to 1 mM. Compound E initially formed fibrils that became more well-defined with time, and after 3 days the fibers laterally coalesced into sheets. Subsequently, these sheets rolled up into nanotubes, which increased in proportion over two weeks. Aqueous solutions of E contained nanotubes of 80-120 nm diameter with 16 nm wall thicknesses, as observed for the dipeptides (FIG. 7).

Compound F showed nanotubes in a diameter of 80-120 nm formed by rolling-up nanoribbons in PBS (FIG. 6, center top), and non-specific aggregation was observed in water with a small degree of sheet formation (FIG. 6, center bottom). In contrast, no nanotubes were formed in pure water even at high concentrations (10 mM) after 2 weeks aging. Short, uniform nanofibers of G formed in PBS (FIG. 6, top right), and no assembly was apparent in pure water (FIG. 6, right bottom).

Overall, the CPT-peptide conjugates tended to slowly assemble into nanostructures or undergo nonspecific aggregation in water, whereas well-defined, nanostructures formed in PBS. The effect of divalent anion of aggregation was investigated by Chen and coworkers (Yang et al., Anion effect on the nanostructure of a metal ion binding self-assembling peptide. *Langmuir* 2006, 22, 8553), which reported that the divalent anion might serve as a bridge by electrostatically interacting with two lysine residues from different peptide molecules, promoting highly defined nanostructures. Divalent anions such as phosphate ions in PBS could accelerate the assembly process of CPT/CPT analog-peptide conjugates by forming a salt bridge.

Example 3: Activity

The conjugates discussed in Examples 1 and 2 were tested for efficacy against killing human colorectal cancer cells in an in vitro cell assay. HT-29 cells were plated into 96-well tissue culture plates, at a density of 5,000 cells/well, and allowed to grow overnight. The conjugates were previously prepared at 10 mM in sterile PBS and allowed to age 3 days, while all other Camptothecin drugs were prepared fresh for each experiment/replicate. Irinotecan HCl was dissolved in pH-neutral, sterile-filtered water, and S-Camptothecin and 10-hydroxycamptothecin were dissolved in DMSO due to solubility issues. Further dilutions of all drugs, both Camptothecin-peptides and free Camptothecin derivatives, were performed in cell culture medium. The cells were then exposed to serial dilutions containing the drugs or cell culture medium alone for the control. A peptide derivative was prepared without Camptothecin to serve as a control to test for toxicity of the peptides themselves, and was also tested in this assay. The cells were then allowed to grow for a further 4 days before being assessed for viability using an MTS colorimetric assay.

FIG. 8 shows the results of the cell culture assay. In general, the active drugs—Camptothecins without modification—were the most potent, while Irinotecan HCl was the least potent. All Camptothecin-peptide assemblies used in these experiments were significantly more potent than Irinotecan HCl.

Due to the UV-fluorescent nature of Camptothecin, confocal microscopy was performed to visualize the drug distribution and internalization within HT-29 cells, as shown in FIG. 9. The top left image shows control cells that were not exposed to either drug, while the top right shows cells exposed to Fmoc-KFKK(CPT)-NH$_2$ (SEQ ID NO:1). Camptothecin in this case is shown as light grey in the images. The bottom left shows the fluorescence image of cells exposed to an identical (200 μM) concentration of Irinotecan HCl.

To quantify the cellular uptake as a function of time, flow cytometry was conducted by monitoring the CPT dipeptides at a wavelength of 420-470 nm after 335 nm excitation. Irinotecan-treated cells consistently had the highest fluorescence for all incubation periods. On the other hand, the CPT-peptide conjugates exhibited time-dependent uptake, with uptake of D being slightly higher than that of C. An analogous flow cytometry study was performed with A549 cells, and similar results and trends were observed.

Example 4: Characterization

Fourier-transform infrared (FTIR) and UV-Vis spectroscopy provided further information on the intermolecular interactions that stabilize the nanotubes. Solutions of C and D, prepared in PBS (20 mM, D20), displayed relatively weak amide I ($v_{C=O}$) bands at 1625 cm$^{-1}$, characteristic of β-sheet secondary structure, and a larger band at 1650 cm$^{-1}$ due to the presence of a random coil conformation. Deconvolution of the spectra indicated that the nanotubes were comprised of 64% random coil and 36% β-sheet structures. The UV-vis spectra of both dipeptides in PBS displayed two bands at 350 and 368 nm that were slightly red-shifted compared with solutions measured in TFE, in which both are minimally aggregated. The lower ratio of the bands at 350 and 368 nm, along with the significantly lower extinction coefficients in PBS compared with TFE, were consistent with the formation of J-aggregated CPT chromophores within the assemblies. These observations indicate that self-assembly is predominantly driven by amphiphilic phase segregation in aqueous media, exhibiting limited β-sheet structure.

The hydrolytic stability of C and D was measured by HPLC in PBS at 37° C. over a week as a function of concentration. In contrast to CPT, which underwent hydrolysis to the inactive carboxylate form within hours in PBS, C and D were present in 91 and 71% of the lactone form after 7 days, respectively, when stored at 10 mM. The stability of the lactone depended strongly on the concentration (FIG. 11(A)). For example, the amount of lactone remaining after 7 days decreased from 91 to 30% for C upon changing the concentration from 10 to 0.2 mM). This progression is consistent with the non-covalent nature of the nanotube structures, which depend on concentration. However, even at 0.2 mM in PBS, 80% of the lactone remained after 24 h, in contrast to CPT, of which 17% of its structure was in the lactone form after 24 h under these conditions.

TEM imaging of samples prepared by diluting C and D (10 mM PBS) to 1 mM with human serum (HS) revealed that the nanotubes were present in HS after 24 h at 1 mM (FIG. 11(B)-(C)). After 30 h at 10 mM in HS at 37° C., C existed predominantly in the lactone form (~89%), whereas D contained ~40% lactone. The values measured between 30-104 h were relatively constant, indicating that equilibrium was attained at 30 h. In contrast, both CPT and Irinotecan were predominantly hydrolyzed after 1-3 h in HS. The lactones of both dipeptides were significantly less stable when the solutions were diluted to 1 mM in HS, similar to the studies in PBS. However, C exhibited significantly greater stability than D.

Example 5: Animal Studies

NH$_2$—KK(CPT)-NH$_2$ (D) was evaluated for efficacy in treating Lewis Lung Carcinoma (LLC) and mesothelioma tumor xenografts in mice. Animals were first injected with tumor cells either into the flank (LLC model; FIG. 12) or peritoneum (mesothelioma model; Table 2)), and allowed to develop small tumors. The animals were subsequently administered weekly either intravenous or intraperitoneal drugs or saline (negative control), and monitored for tumor burden and body weight over several weeks. These studies indicate lower in vivo efficacy of the nanotubes. But these initial studies were extremely limited in scope, only testing one of 15-20 structures that have been created. This lower efficacy is most likely due to reduced mobility of the 1D nanotubes within tissue, a property that can be beneficially exploited to increase the retention of drug within tumors by allowing the assembly process to respond structurally in the environment of the tumor cells.

TABLE 2

MSTO Model

| | Treatment Group (dose) | | | |
| --- | --- | --- | --- | --- |
| | Irinotecan (100 mg/kg) | S-CPT (5 mg/kg) | Nano-CPT (5 mg/kg) | Nano-CPT (15 mg/kg) |
| Deaths from Tumor Burden | 0/5 | 0/5 | 2/5 | 2/5 |

Example 6: Synthesis 5-FU-peptides

Two 5-Fluorouracil (5-Fu) peptide conjugates were synthesized using two different linkages, amide and ester, to connect 5-Fu with dipeptide. For amide linkage, a 5-Fu acetic acid linker was synthesized by reacting 5-Fu with chloroacetic acid in KOH solution. For the ester linkage, 5-Fu succinic acid was synthesized by reacting 1,3-dimethylol-5-fluorouracil with benzyl succinate. The benzyl protecting group was removed later with 10% Pd/C and Hz. Both 5-Fu derivatives were reacted with lysine amine side chain to form amide or ester bond using the standard amide formation method (HBTU, DIPEA). The peptide synthesis achieved manually with Fmoc/t-Bu solid-phase peptide synthesis on rink amide resin and was purified by RP-HPLC. The synthesis scheme is shown below:

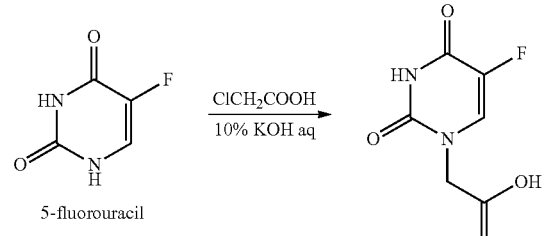
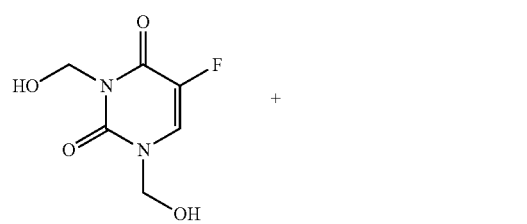
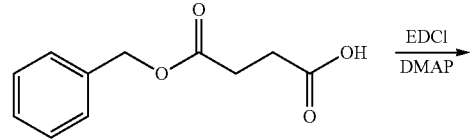
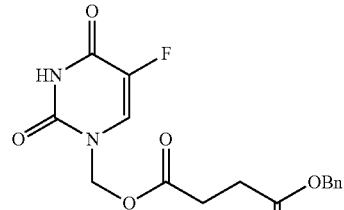
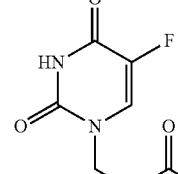
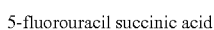
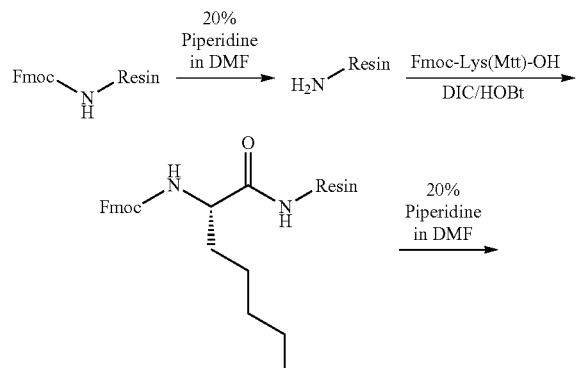
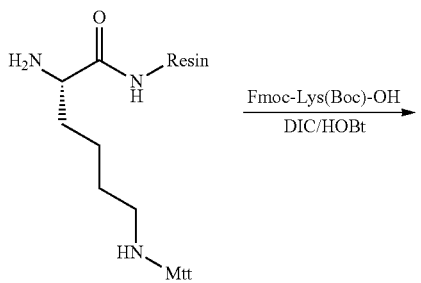
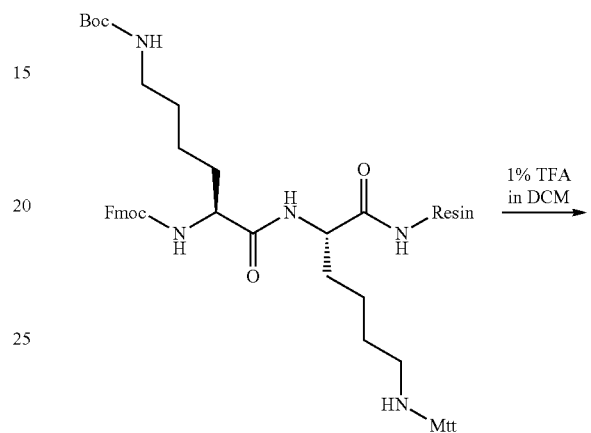
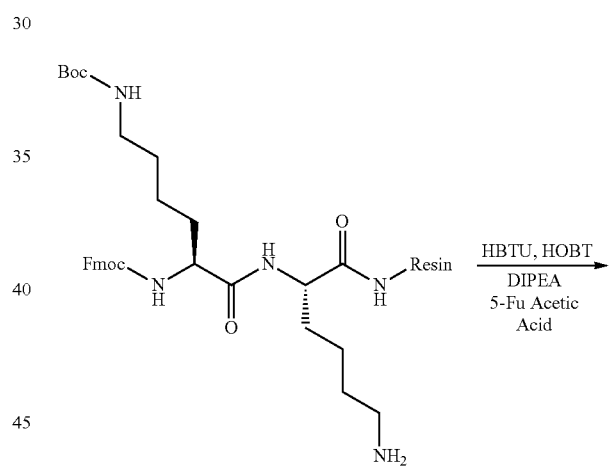
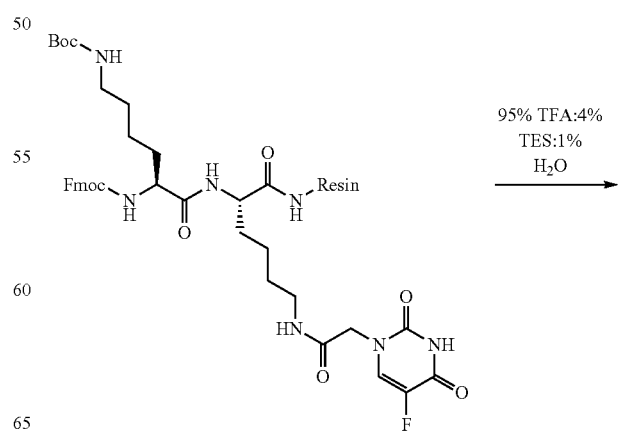

-continued

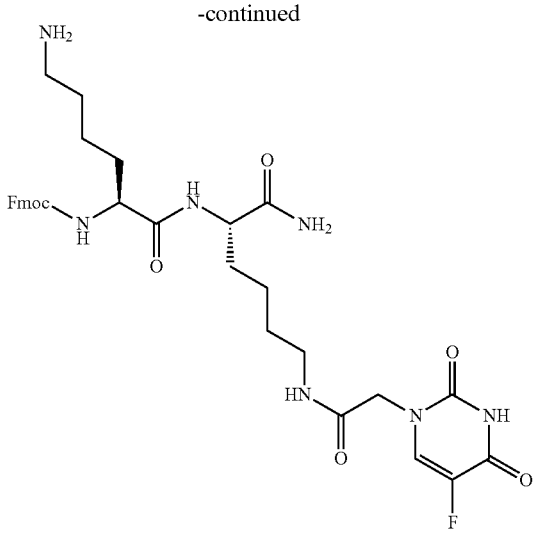

The morphologies of two 5-Fu peptide conjugates were investigated by TEM in PBS (pH 7.4). 5-Fu peptide conjugate samples in PBS (10 mM, pH 7.4) was prepared and aged for 1 day before the measurement. The sample was freshly diluted in PBS to 1 mM before taking TEM pictures. 10 µL drops of sample solution in PBS (1 mM) were applied to carbon coated copper grid (Ted Pella, Inc) for 2 min. After removal the excess solution with filter paper, the grid was floated on 10 µL drops of 2% wt uranyl acetate solution for negative stain for 1 min TEM pictures of 5-Fu acetic acid conjugate shows uniform nanofiber structure in PBS solution with the length over 500 nm (FIG. 13).

The materials and methods of the appended claims are not limited in scope by the specific materials and methods described herein, which are intended as illustrations of a few aspects of the claims and any materials and methods that are functionally equivalent are within the scope of this disclosure. Various modifications of the materials and methods in addition to those shown and described herein are intended to fall within the scope of the appended claims. Further, while only certain representative materials, methods, and aspects of these materials and methods are specifically described, other materials and methods and combinations of various features of the materials and methods are intended to fall within the scope of the appended claims, even if not specifically recited. Thus a combination of steps, elements, components, or constituents can be explicitly mentioned herein; however, all other combinations of steps, elements, components, and constituents are included, even though not explicitly stated.

What is claimed is:

1. A nanotube comprising a wall, wherein the wall comprises a plurality of conjugates of Formula II

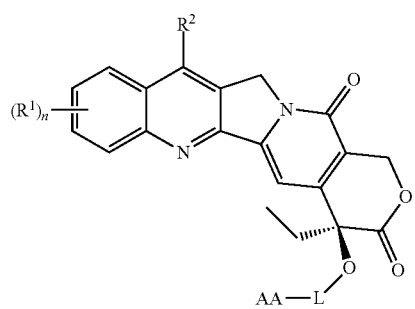

where n is from 1 to 4, each $R^1$ and $R^2$ are, independent of one another, H, OH, lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen or deuterium, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, $N_3$, SH, $SCH_3$, $C(O)CH_3$, $CO_2CH_3$, or $CO_2H$, or together two $R^1$ or $R^1$ and $R^2$ can form a fused cycloalkyl or cycloheteroalkyl;

L is $C(O)-(CH_2)_m-C(O)$, where m is from 1 to 6;

AA is a protected or unprotected lysyl-lysyl or lysyl-phenylalanyl-lysyl-lysyl (SEQ ID NO:6); wherein L is bonded at a side chain of one of the lysyl residues of AA.

2. The nanotube of claim 1, wherein the wall comprises a hydrophilic domain comprising the AA moiety of the conjugate and a hydrophobic domain comprising the

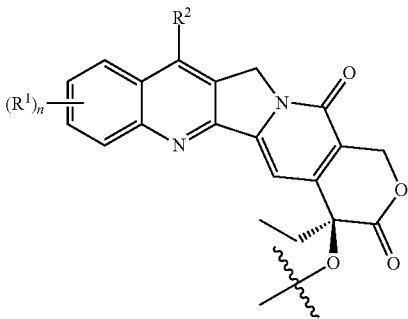

portion of the conjugate.

3. The nanotube of claim 1, wherein the

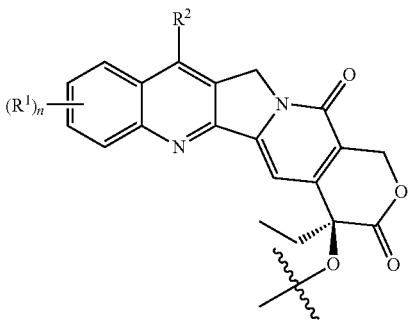

portion of the conjugate is at least about 50 wt. % of the nanotube.

4. The nanotube of claim 1, wherein the nanotube has a zeta potential of about zero mV.

5. The nanotube of claim 1, wherein AA is protected at the N terminus or an amino acid residue side chain with a benzoyloxycarbonyl, tert-butoxycarbonyl, acetate, trifluoroacetate, 9-fluorenylmethyloxycarbonyl, or 2-bromobenzyloxycarbonyl, or N-hydroxysuccinimide.

6. The nanotube of claim 1, wherein AA is unprotected lysyl-lysyl, or unprotected lysyl-phenylalanyl-lysyl-lysyl (SEQ ID NO:6), and the linker moiety is $C_1$-$C_6$ alkyldiester.

7. The nanotube of claim 1, wherein the conjugate has Formula II-A, II-B, II-C, II-D, or II-E:

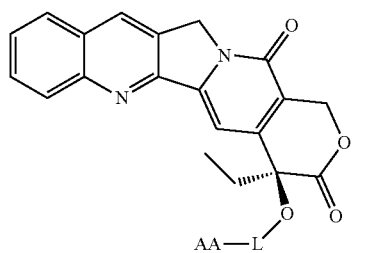
II-A
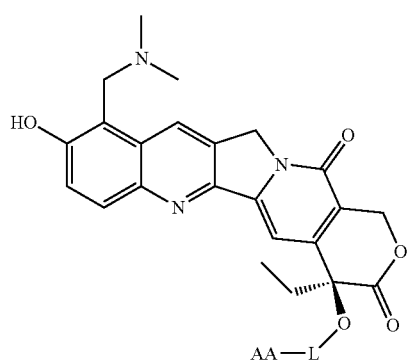
II-B
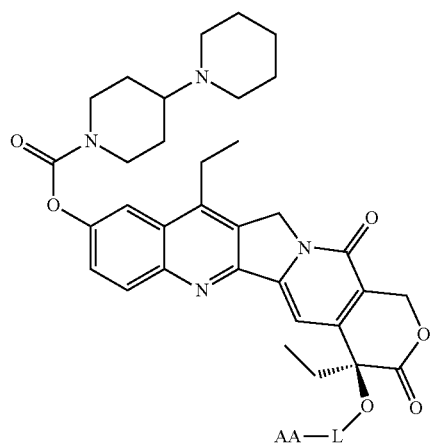
II-C
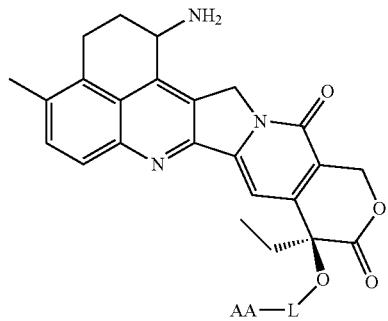
II-D
II-E
* * * * *